United States Patent
Mano et al.

(10) Patent No.: US 9,617,577 B2
(45) Date of Patent: Apr. 11, 2017

(54) BACILLUS PUMILUS BILIRUBIN OXIDASE AND APPLICATIONS THEREOF

(71) Applicant: CENTRE NATIONAL DE LA RECHERCHE SCIENTIFIQUE, Paris (FR)

(72) Inventors: Nicolas Mano, Talence (FR); Fabien Durnad, Bordeaux (FR)

(73) Assignee: CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 167 days.

(21) Appl. No.: 14/528,583

(22) Filed: Oct. 30, 2014

(65) Prior Publication Data

US 2015/0096903 A1    Apr. 9, 2015

Related U.S. Application Data

(62) Division of application No. 13/636,960, filed as application No. PCT/IB2011/051258 on Mar. 24, 2011, now abandoned.

(30) Foreign Application Priority Data

Mar. 24, 2010    (FR) ...................................... 10 01167

(51) Int. Cl.
  *C12Q 1/00*    (2006.01)
  *H01M 8/16*    (2006.01)
  *C12N 9/02*    (2006.01)
  *C12Q 1/26*    (2006.01)
  *H01M 4/90*    (2006.01)

(52) U.S. Cl.
  CPC ............. *C12Q 1/005* (2013.01); *C12N 9/001* (2013.01); *C12Q 1/26* (2013.01); *C12Y 103/03005* (2013.01); *H01M 4/90* (2013.01); *H01M 8/16* (2013.01); *Y02E 60/527* (2013.01)

(58) Field of Classification Search
  None
  See application file for complete search history.

(56) References Cited

PUBLICATIONS

Accession A8FAG9. Nov. 13, 2007.*
Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner* — Christian Fronda
(74) *Attorney, Agent, or Firm* — B. Aaron Schulman, Esq.; Stites & Harbison, PLLC.

(57) ABSTRACT

The present invention relates to a novel *Bacillus pumilus* bilirubin oxidase, to the method for preparing same and also to the use thereof in particular for assaying bilirubin and for using enzymatic biofuel cells.

13 Claims, 9 Drawing Sheets

BACILLUS PUMILUS BILIRUBIN OXIDASE AND APPLICATIONS THEREOF

This application is a Divisional of U.S. patent application Ser. No. 13/636,960, having a filing date of Dec. 10, 2012, which is a 371 application of PCT/IB2011/051258, filed Mar. 24, 2011, all of said applications herein incorporated by reference.

The present invention relates to a novel bilirubin oxidase, to the method for preparing same and also to the use thereof in particular for assaying bilirubin and for the use of enzymatic biofuel cells using oxygen as fuel.

Bilirubin oxidase or BOD (E.C. 1.3.3.5.) is an enzyme which catalyses the reaction for oxidation of bilirubin to biliverdin:

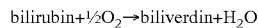

BOD has four sites for binding to copper atoms; these four copper atoms are necessary for correct activity of the enzyme; it has in fact been shown that the absence of a copper in the CotA protein of *Bacillus subtilis* (a protein with bilirubin oxidase activity sold, as BOD, by the company Genzyme Diagnostics) is sufficient to reduce the activity of the enzyme (table 3 of the article by Durao et al., in J Biol Inorg Chem. 2008 February; 13(2): 183-93).

Bilirubin is a yellow substance formed in the blood by the decomposition of haemoglobin; it is one of the main pigments produced in the liver.

BOD is of interest for various applications, such as the assaying of bilirubin, making it possible, for example, to diagnose excess bilirubin in the blood; it can also be used to prepare enzymatic biofuel cells where it will capture cathode electrons, reducing oxygen to water (see the schematic representation of an enzymatic biofuel cell where the BOD is attached in a redox polymer to the cathode, in FIG. 1A) or as an oxygen biosensor.

There are many sources of BOD; this enzyme can be produced from microorganisms such as those of the *Bacillus* genus [*Bacillus subtilis*, the CotA of which has a bilirubin oxidase activity, see Sakasegawe et al. 2006 Applied and Environmental Microbiology 72, No. 1, 972-975; *Bacillus licheniformis* (U.S. Pat. No. 4,770,997)], or from mycetes, among which, those of the genus *Penicillium* [*Penicillium janthinellum* (patent application EP 0 295 101)], Trachyderma (U.S. Pat. No. 4,600,689), *Myrothecium* (Tanaka et al. 1982 Agric. Biol. Chem. 46, 2499-2503) or else *Schizophyllum, Coprinus, Trametes, Coriolus, Pholiota, Pleurotus, Lenzites* or *Fomitopsis* (U.S. Pat. No. 4,677,062).

This enzyme can also be extracted from plants such as of the type Alfalfa (U.S. Pat. No. 5,624,811), Solanaceae, Musaceae and Liliaceae (EP 0 140 004) or else Compositae, such as the artichoke (EP 0 247 846).

Among these enzymes, the BODs having the most advantageous enzymatic properties, in particular activity and stability, have been selected to be marketed; they are *Bacillus subtilis* CotA having bilirubin oxidase activity (it is sold as BOD by the company Genzyme Diagnostics and will subsequently be denoted BOD) and *Myrothecium verrucaria* BOD (sold by the companies Sigma-Aldrich and Amano).

The inventors have now identified a novel BOD produced by *Bacillus pumilus* which is more active and/or more stable than the commercially available BODs; they have also developed a method for preparing this novel BOD which is simpler and faster than those used to date for the other known BODs.

According to a first subject, the invention relates to the wild-type BOD of *Bacillus pumilus*; in particular, the bilirubin oxidase, in particular the purified bilirubin oxidase (purity>95%) according to the invention has a percentage identity of at least 80%, and by order of increasing preference at least 85%, 90%, 95%, 97%, 98% and 99% identity, with respect to the wild-type BOD of *Bacillus pumilus* of SEQ ID No. 2; it catalyses the reaction for oxidation of bilirubin to biliverdin and is bound to four copper atoms.

SEQ ID No. 2 corresponds to the wild-type BOD of the *Bacillus pumilus* strain SAFR032. By way of example, the present invention also relates to the wild-type BODs of other *Bacillus pumilus* strains, for instance the BOD of the ATCC 7061 strain of SEQ ID No. 6, which has a percentage identity of 98% with the BOD of SEQ ID No. 2; the preferred BOD according to the invention is the wild-type BOD of the *Bacillus pumilus* strain SAFR032 of SEQ ID No. 2.

The identity of a sequence with respect to the sequence of the wild-type BOD of *Bacillus pumilus* (SEQ ID No. 2) as reference sequence is assessed according to the percentage of amino acid residues which are identical, when the two sequences are aligned, so as to obtain the maximum correspondence between them.

Protein sequences predicted from the systematic sequencing of the *Bacillus pumilus* genome are described in the UniProt database (accession number A8FAG9 "Outer Spore Coat Protein A" of 13 Nov. 2007 and accession number B4AIB1 "Spore Coat Protein A" of 23 Sep. 2008); it should be underlined that the information presented in the UniProt database is predictive and putative, it does not result from the experimental isolation and characterization of *Bacillus pumilus* proteins. In addition, the indications appearing in this database did not make it possible to predict any BOD activity for these proteins, since, among the various CotA characterized to date from the organisms *B. subtilis, B. licheniformis* (Koschorreck, K., et al., Cloning and characterization of a new laccase from *Bacillus licheniformis* catalysing dimerization of phenolic acids. Appl Microbiol Biotechnol, 2008. 79(2): p. 217-24; Koschorreck, K., R. D. Schmid, and V. B. Urlacher, Improving the functional expression of a *Bacillus licheniformis* laccase by random and site-directed mutagenesis. BMC Biotechnol, 2009. 9: p. 12), *B. halodurans*, and *B. HR*03, before the BOD of *B. pumilus*, only that of *B. subtilis* has been characterized as a BOD, the others being laccases (enzymes having a weak tetrapyrrole-oxidizing activity, unlike BODs).

The percentage identity can be calculated by those skilled in the art using a sequence comparison computer program such as, for example, that of the BLAST series (Altschul et al., NAR, 25, 3389-3402). The BLAST programs are implemented on the window of comparison consisting of the entire SEQ ID No. 2 indicated as reference sequence.

A peptide having an amino acid sequence having at least X % identity with a reference sequence is defined, in the present invention, as a peptide of which the sequence can include up to 100-X modifications per 100 amino acids of the reference sequence, while retaining the functional properties of said reference peptide, in the case in point its bilirubin oxidation enzymatic activity. For the purpose of the present invention, the term "modification" includes consecutive or dispersed deletions, substitutions or insertions of amino acids in the reference sequence.

The novel BOD according to the invention has improved properties compared with the commercially available BODs derived from *Myrothecium verrucaria* or *Bacillus subtilis*.

In particular, the *Bacillus pumilus* BOD has better enzymatic properties (activity, catalytic efficiency $k_{cat}$ and affinity of the substrate for the enzyme $K_M$) with respect to catalysis of the oxidation of 2,2'-azinobis(3-ethylbenzothiazoline-6-sulphonic acid) (ABTS), than the BODs of *Myrothecium verrucaria* or of *Bacillus subtilis*.

The enzymatic properties can be determined as described in part 4 of the example which follows.

Table I below gives the catalytic efficiency $k_{cat}$, i.e. the number of molecules of substrate converted to product per molecule of enzyme and per unit time, and the Michaelis constant $K_M$ which represents the affinity of the substrate (ABTS) for the BODs of *B. subtilis* and of *B. pumilus*.

The enzymatic properties of the BODs of *B. pumilus* and of *B. subtilis* can easily be compared since these two enzymes have very similar optimal conditions for use: pH between 3 and 4 and temperature between 75 and 80° C.

TABLE I

Enzymatic properties of the BODs of *B. pumilus* and of *B. subtilis*

| BOD | $k_{cat}$ (for ABTS) | $K_M$ |
|---|---|---|
| *B. pumilus* | 391.3 s$^{-1}$ | 31.7 μM |
| *B. subtilis* | 322 s$^{-1}$ | 124 μM |

The enzymatic properties described for the *M. verrucaria* BOD by Kataoka et al. (2005, Protein Expression and Purification, 41, 77-83) at pH 6.5 are a $k_{cat}$ of 115 s$^{-1}$ and a $K_M$ of 250 μM. Moreover, Sakurai et al. (2008, Biochemical and Biophysical Research communication, 371, 416-419) have determined the specific activity of the *M. verrucaria* BOD for ABTS, which is 106 U/mg, the specific activity of the BOD according to the invention itself being 375 U/mg.

In addition, the *B. pumilus* BOD has very good heat stability and good bilirubin oxidation enzymatic properties.

The present invention also relates to a nucleic acid molecule encoding the BOD according to the invention; it is preferably a nucleic acid molecule having a sequence chosen from SEQ ID. No. 1 encoding the wild-type BOD of *Bacillus pumilus* SARF-032, SEQ ID No. 5 encoding the wild-type BOD of *Bacillus pumilus* ATCC 7061 or else SEQ ID No. 7 which corresponds to the sequence of the wild-type BOD of *Bacillus pumilus* SARF-032 which has been modified in order to improve the expression thereof by the yeast *Pichia pastoris*.

The nucleic acid molecule encoding the BOD according to the invention can be cloned into an expression vector, such as a plasmid, and then used to transform a suitable host, such as a bacterium, a yeast or else a cell culture.

The term "expression vector" is intended to mean a vector which has a region allowing the insertion of a coding nucleotide sequence between the signals essential for its expression, in particular a promoter (constitutive or inducible), a ribosome-binding site, a transcription stop signal and, optionally, a selectable marker, such as a gene for resistance to an antibiotic.

The present invention also relates to an expression vector comprising said nucleic acid molecule and to a host cell transformed with said expression vector and expressing a BOD according to the invention.

The introduction of the expression vector into the host cell can be carried out by any method known to those skilled in the art, in particular by a modification of the membrane permeability of the host cell, for example in the presence of calcium ions, or by electroporation.

After culture of the host cells transformed so as to express the BOD according to the invention, said cells can be recovered by centrifugation, and lysed in order to release the enzymes, including said BOD according to the invention.

If *Escherichia coli* is the host microorganism, the plasmids which can be used are in particular the plasmids pBluescript, pUC18, pET, pGEX, pGS, pMAL-c2, or the like.

According to a preferred method for preparing the BOD according to the invention, the BOD is expressed by an *E. coli* bacterium transformed with a pET21a expression vector encoding an enzyme joined to a 6HIS tag in the C-terminal position.

This method, illustrated in the experimental section which follows (section 3), is advantageous owing to its rapidity and its simplicity; this is because the induction of the *Bacillus pumilus* BOD expression in the *E. coli* bacterium takes place in 4 to 24 hours, whereas the production of BOD derived from *Myrothecium verrucaria* requires induction periods that can reach 5 days (Kataoka et al. Biochemistry. 2005 May 10; 44(18):7004-12; Kataoka et al., Biochem Biophys Res Commun. 2008 Jul. 4; 371(3):416-9; Kataoka et al. K. Protein Expr Purif. 2005 May; 41(1):77-83).

In addition, the 6HIS tag makes it possible to purify the *Bacillus pumilus* BOD by affinity chromatography on a nickel resin in a single step so as to obtain a pure enzyme; the small size of the tag (6 amino acids) makes it possible to do away with eliminating it since it does not significantly disturb the activity of the enzyme. By way of comparison, the purification of the *Myrothecium verrucaria* and *B. subtilis* BODs which is described, respectively, in the articles by Kataoka et al. (see above) and Durao et al. (J Biol Inorg Chem. 2008 February; 13(2):183-93) require several chromatography steps.

The rapidity and the simplicity of this method therefore represent considerable advantages compared with the methods for preparing enzymes that are currently commercially available. Those skilled in the art will select the host cell according to the expression vector used.

Preferably, when the pET21a expression vector is used, a host cell expressing the T7 RNA polymerase, such as the *E. coli* strains BL$_{21}$ DE3, BL$_{21}$-SI, BL$_{21}$ pLys, Novablue (DE3) or BL$_{21}$ Star, will be selected.

Preferably, the *Bacillus pumilus* BOD according to the invention is produced in an *Escherichia coli* BL$_{21}$ Star strain; the nucleic acid molecule which encodes it is obtained by PCR with the primers of SEQ ID Nos. 3 and 4 and cloned into the pET21a vector so as to give the transformed vector pFD1. The BOD thus produced is then purified, after lysis of the bacteria, by affinity chromatography.

According to another advantageous variant of the invention, the BOD according to the invention is produced by the *Pichia pastoris* yeast.

In order to allow the overproduction and the secretion of the BOD into the culture medium of the *Pichia pastoris* yeast, the gene encoding the BOD, in particular chosen from the sequences SEQ ID No. 1, 5 or 7, preferably SEQ ID No. 7, is introduced by homologous recombination into the yeast genome, at the level of the AOX1 gene. For this, the pFD2 plasmid, once linearized by digestion with the pmeI enzyme, is introduced into the yeast by electroporation, and the positive clones are selected on YPD+agar medium containing zeocin at 100 μg/ml. A preculture of 200 ml of YPD medium supplemented with zeocin (100 μg/ml) is inoculated using an isolated clone on a Petri dish. After shaking at 220 rpm overnight at 30° C., this preculture is then centrifuged for 10 min at 4000 rpm and the pellet is taken up in 200 ml of sterile water in order to remove any presence of glucose.

After a second centrifugation, a 2 L culture in MMH medium containing 1 mM of $CuSO_4$ in a 5 L Erlenmeyer flask is then inoculated with this pellet. The yeasts are incubated at 25° C. with shaking (220 rpm) for 2 hours, before the addition of 0.5% of methanol in order to initiate the induction. This induction step will be repeated for 5 days in order to obtain the maximum amount of enzymes.

In order to implement this method, the following material can be used, without being limiting in nature:
  vector for expression in *Pichia pastoris* (pFD2): pPICZα plasmid containing the DNA sequence encoding the *Bacillus pumilus* BOD, preferably optimized (SEQ ID No. 7), in frame with the *Saccharomyces cerevisiae* α-factor secretion factor and containing the methanol-inducible AOX1 promoter;
  *Pichia pastoris* yeast strain GS115 used for producing bilirubin oxidase after integration of the cassette derived from the PFD2 vector containing the AOX1 promoter, the α-factor signal peptide and the DNA sequence encoding the *Bacillus pumilus* BOD;
  culture media:
YPD Rich Medium (for Yeast):
  1% yeast extract
  2% bactopeptone
  2% glucose
  pH not adjusted, autoclaved for 20 min at 120° C.
MMH Minimum Medium (for Yeast):
  1.34% yeast nitrogen base
  1% Casamino acid
  0.4% histidine
  $4 \times 10^{-5}$% biotin
  pH not adjusted, autoclaved for 20 min at 120° C.
LB Rich Medium (for Bacterium):
  10 g/l tryptone
  5 g/l yeast extract
  5 g/l NaCl
  Distilled $H_2O$ qs 1l
  pH not adjusted, autoclaved for 20 min at 120° C.

The present invention also relates to a method for preparing a BOD according to the invention, comprising the steps of:
  a) preparing host cells expressing the BOD according to the invention;
  b) culturing the host cells prepared in step a);
  c) lysing the host cells;
  d) treating the lysate obtained in step c) by affinity chromatography;
  e) recovering said purified BOD.

According to one preferred embodiment, the method according to the invention is such that:
  the *Escherichia coli* $BL_{21}$ Star strain transformed with the pFD1 vector is prepared in step a);
  the culture carried out in step b) is a liquid-phase culture, with shaking, under anaerobic conditions for a period of 4 to 30 h, preferably 24 h, at a temperature between 18 and 37° C., preferably 20° C., during which the BOD expression is induced by adding isopropyl-β-D-1-thiogalactopyranoside (IPTG). When the method is implemented according to these preferred conditions, it allows the production of the BOD with a short induction time, of about 24 hours; the purification of the BOD is carried out in a single affinity chromatography step and the BOD thus produced indeed comprises the four copper atoms necessary for its activity (see part 5 of the example).

It is also possible to produce a BOD in the presence of denaturing agents such as urea, guanidinium chloride, SDS, triton, etc., the BOD thus produced will then be devoid of copper and may be activated by adding copper ions.

The invention also relates to the use of the *Bacillus pumilus* BOD according to the invention for assaying bilirubin in solution, i.e. measuring the bilirubin concentration in a sample, in particular a biological sample.

The term "biological sample" is intended to mean a biological fluid, such as blood, serum, lymph, bile, urine, cerebrospinal fluid, sweat, etc.

The presence of bilirubin in the organism is normal, it comes from the degradation of haemoglobin and approximately 200 to 230 mg of bilirubin are formed per day in a healthy adult. In an individual in good health, the bilirubin is taken up by the liver and then degraded; its concentration should not therefore exceed certain thresholds, and the assaying of bilirubin is useful for detecting pathological conditions such as:
  cases of substantial haemolysis: congenital or acquired haemolytic anaemia, drug-related, toxic or infectious haemolysis, transfusion accidents, etc.;
  insufficient hepatic uptakes or conjugations: Gilbert disease, Criggler-Najjar disease, the taking of rifampicin (antitubercular antibiotic);
  hepatic and biliary conditions: the various types of hepatitis (viral, toxic, drug-related), the various types of cirrhosis, rare metabolic abnormalities (Rotor's disease, Dubin-Johnson disease);
  biliary conditions;
  biliary lithiasis;
  pancreatitis;
  pancreatic or bile duct cancer.

The present invention thus relates to the use of the BOD according to the present invention for measuring the bilirubin concentration in a liquid sample, in particular a biological sample.

According to a first variant, the principle of the assaying of bilirubin with BOD is based on measuring the change in colour of the sample caused by the degradation of the bilirubin.

Bilirubin exhibits a light absorption peak ($\lambda_{max}$) at 440 nm; when it is enzymatically degraded by a BOD, the absorbance at $\lambda_{max}$ of the sample in which it is present decreases; this decrease makes it possible to quantify the bilirubin initially present in the sample by comparison with the decrease in absorbance at 440 nm of calibration solutions containing known bilirubin contents measured under the same experimental conditions.

The present invention also relates to a kit for assaying bilirubin in solution, characterized in that it comprises a BOD according to the invention.

Typically, the assaying kit also contains the reagents necessary for carrying out the bilirubin assay test, in particular:
  the buffers;
  the standard solutions of bilirubin for producing calibration curves, and
  the set of instructions necessary for carrying out the assay.

The present invention also relates to a method for assaying the bilirubin in solution in a liquid sample, characterized in that it comprises the following steps:
  a) measuring the absorbance at $\lambda_{max}$=440 nm of said liquid sample before enzymatic reaction;
  b) introducing a BOD according to the invention into said liquid sample;
  c) measuring the absorbance at $\lambda_{max}$=440 nm of said liquid sample after enzymatic reaction;

d) calculating the difference in absorbances measured in steps a) and c) and comparing this difference with differences in absorbances measured for standard solutions having a known bilirubin content;

e) determining the initial concentration of bilirubin of said liquid sample.

According to another variant, the assaying of the bilirubin in a liquid sample is carried out by means of an electrochemical method which uses an electrode including the BOD according to the invention.

Thus, the present invention also relates to BOD electrodes comprising a conductive material, such as a conductive metal, in particular platinum, copper, silver, aluminium, gold or steel, or carbon, for instance vitreous carbon, carbon fibres, fibres of carbon nanotubes or alternatively which are made of diamond, etc., said conductive material being coated with a deposit comprising at least one BOD according to the invention, it also being possible for said deposit to comprise a redox polymer in order to improve the electrical conduction between the enzyme and the electrode and also the stability of the system.

The redox polymer can, for example, be chosen from ferrocene-based, osmium-based and ruthenium-based polymers and conducting polymers such as, for example, polypyrrole and polyanaline.

The methods for immobilizing the BOD on said conductive material can be chosen from the conventional methods available to those skilled in the art, which comprise, in particular, embedding of the BOD in a polymer matrix, adsorption of the BOD at the surface of the polymer membrane, attachment by covalent bonding, electrodeposition (Gao et al., Chem. Int. ED. 2002, 41, No. 5, 810-813) or else the technique described in United States patent application US 2009/0053582.

According to one embodiment variant, the BOD electrode on which the BOD is immobilized is also coated with a membrane which prevents the detachment of said enzyme from the electrode. According to the applications envisaged, said membrane can be constituted of nafion, of cellulose or of any other biocompatible material, i.e. material compatible with a physiological environment.

The present invention thus also relates to a bilirubin biosensor constituted of a BOD electrode according to the invention. Generally, a biosensor consists of an electrode on which a bioreceptor capable of recognizing a biological target is immobilized; the binding of the biological target to the bioreceptor results in physicochemical modifications of the membrane and the production of an electrical signal by an electrochemical (amperometric, potentiometric, conductometric, etc.) transducer joined to the electrode. In the present case, the biosensor is a BOD according to the invention and the biological target is bilirubin.

The present invention also relates to a method for assaying bilirubin in solution in a liquid sample with a bilirubin biosensor according to the invention.

According to one variant of use of the bilirubin biosensor, the latter is implanted under the skin of an individual and makes it possible to record the bilirubin concentration in the blood of said individual.

The present invention also relates to an oxygen sensor constituted of an electrode according to the invention.

The BOD electrode according to the invention can also be advantageously used as a cathode in an enzymatic biofuel cell;

FIG. 1A represents schematically the operating principle for an enzymatic biofuel cell. The enzymatic biofuel cells according to the invention are devices comprising a BOD electrode as a cathode and an anode where a substrate oxidation reaction takes place (catalysed by the "enzyme X"); by way of illustration, the substrate may be glucose and the "enzyme X" glucose oxidase; such a cell is of particular interest when the biofuel cell is implanted in an individual for a medical application. The substrate can also be chosen, for example, from nitrites, nitrates, sulphides, urates, ascorbates, glutamates, pyruvates, lactates, cellulose, etc., if an application in depollution is envisaged; the choice of the enzyme will then be made according to the substrate to be degraded; by way of example, the following enzymes can be used, the type of substrate that they can degrade is mentioned between parentheses: glucose oxidase (glucose or any sugars that are oxidized by this enzyme), lactate oxidase (lactate), pyruvate oxidase (pyruvate), alcohol oxidase (alcohol), cholesterol oxidase (cholesterol), glutamate oxidase (glutamate), pyranose oxidase (pyranose), choline oxidase (choline), cellobiose dehydrogenase (cellobiose), glucose dehydrogenase (glucose or any sugars that are oxidized by this enzyme), pyranose dehydrogenase (pyranose), fructose dehydrogenase (fructose), aldehyde oxidase (aldehyde), gluconolactone oxidase (gluconolactone), alcohol dehydrogenase (alcohol), ascorbate oxidase (oxygen or ascorbate) or else sulphide dioxygenase (sulphide). The concomitant oxidation and reduction process at the electrodes of the biofuel cell produces an electric current.

FIG. 1B illustrates more specifically a glucose-based enzymatic biofuel cell; such an enzymatic biofuel cell consists of two electrodes modified by the immobilization of enzymes. A glucose oxidase (GOx) is attached to the anode (1) by means of a conducting polymer "I" and a bilirubin oxidase (BOD) is attached to the cathode (2) by means of a conducting polymer "II". In operating mode, at the anode, the electrons are transferred from the glucose present in the physiological fluid to the GOx, then from the GOx to the conducting polymer "I" and from the conducting polymer "I" to the anode. At the cathode, the electrons are transferred from the cathode to the conducting polymer "II", then to the BOD and, finally, from the BOD to the oxygen present in the physiological fluid.

It should be noted that a biofuel cell can also optionally operate by modifying the electrodes with their respective enzymes and adding soluble mediators, such as ferrocenemethanol for the anode and potassium ferricyanide for the cathode, and adding, as appropriate, a membrane separating the anode and the cathode.

According to another aspect, the present invention relates to the use of a BOD according to the invention for degrading the bilirubin present in a sample, in particular a biological sample. This is because the presence of bilirubin in a sample is capable of distorting the detection of other substances (such as blood glucose or blood cholesterol) in particular when these other substances are detected by a colorimetric method. Generally, the BODs according to the invention have many industrial applications, in particular in the textile and paper industries and in the food sector, in order, for example, to improve the stability and/or the quality of foods, such as beverages, or else foods containing vegetable oils, by deoxygenation.

More specifically, the BODs can be used for applications related to depollution; by way of example, mention may be made of the discoloration or the detoxification of wastewater and the degradation of xenobiotics; as organic synthesis reactants; for the preparation of antimicrobial compositions; for the production of articles made of wood and of cartons which have been detoxified or else for the production of detergent (Morozova et al. Biochemistry (Mosc.) 2007 October; 72(10):1136-50) and for the discoloration of dyes used in industrial media.

The BOD according to the invention can also be used for dimerizing phenolic acid (Koschorreck, K., et al. 2008. Appl Microbiol Biotechnol (2008) 79:217-224) and thus is of interest in the synthesis of pigments and dyes used in textile and food applications (R. Mustafa et al. Food Research International. Volume 38, Issues 8-9, October-November 2005, pages 995-1000); this dimerization reaction can also be used for the preparation of antioxidant compounds, for instance ferulic acid dimers (Garcia-Conesa M T, et al. Redox Rep. 1997 October-December; 3(5-6):319-23).

The BOD according to the invention can also be used as a reactant in a composition for the oxidation dyeing of keratin fibres, such as a hair-dyeing composition, comprising, in a medium suitable for dyeing, at least one oxidation base, a BOD according to the invention and, optionally, a donor for said BOD (such as a substrate, for instance bilirubin). The various ingredients, other than the BOD, that can be used in said composition are described in international application WO 99/15138; by way of example, the oxidation base(s) can be chosen from para-phenylenediamines, double bases, para-aminophenols, ortho-aminophenols and heterocyclic oxidation bases.

The BOD according to the invention can advantageously be used for treating wood pulp for its action on lignin degradation and/or for producing a paper which has a better wet strength (see international application WO 00/68500).

In addition to the above arrangements, the invention also comprises other arrangements which will emerge from the description that follows, which refer to exemplary embodiments of the present invention, and also to the appended figures in which:

FIGURES

EXAMPLE

1. Materials

1.1 *Escherichia coli* Bacterial Strains

DH$_5\alpha$: supE44, ΔlacU169, (Φ80 lacZDM15), hsdR17, recA1, endA1, gyrA96, thi-1, relA1 (Hanahan, 1983).

This strain is used to amplify plasmids during the steps for constructing the protein expression vectors.

BL$_{21}$ Star: F-ompT hsdSB(rB-, mB-) gal dcm rne131 (DE3) (Invitrogen).

This strain is used to produce the *Bacillus pumilus* BOD in Erlenmeyer flasks.

This strain is then transformed with the pFD1 plasmid which contains the DNA sequence encoding the *Bacillus pumilus* BOD under the control of the T7 promoter in the pET21a vector.

1.2 Vector pFD1: pET21a plasmid containing the nucleic acid sequence SEQ ID No. 1 encoding the *Bacillus pumilus* BOD cloned in-frame with the 6×His tag in the C-terminal position.

Figure 1A:
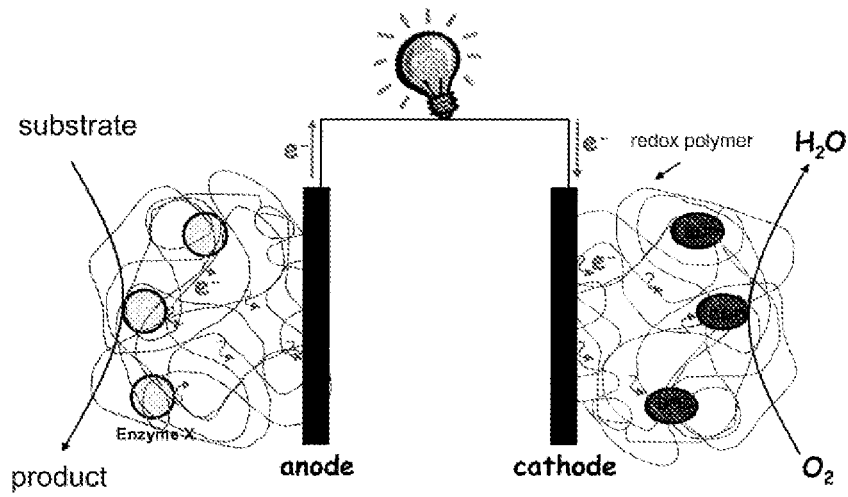
FIG. 1A represents schematically the operating principle for an enzymatic biofuel cell.
Figure 1B:
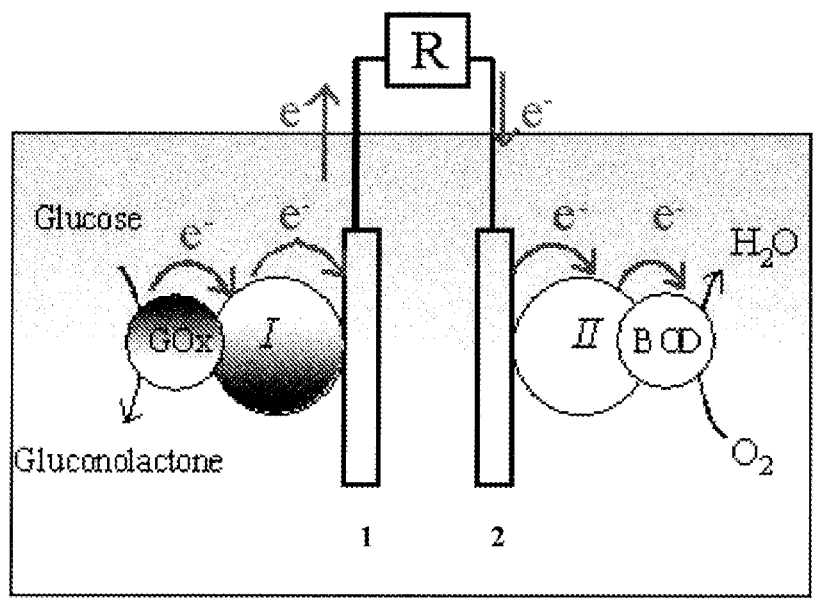
FIG. 1B represents a glucose-based enzymatic biofuel cell.
Figure 2:
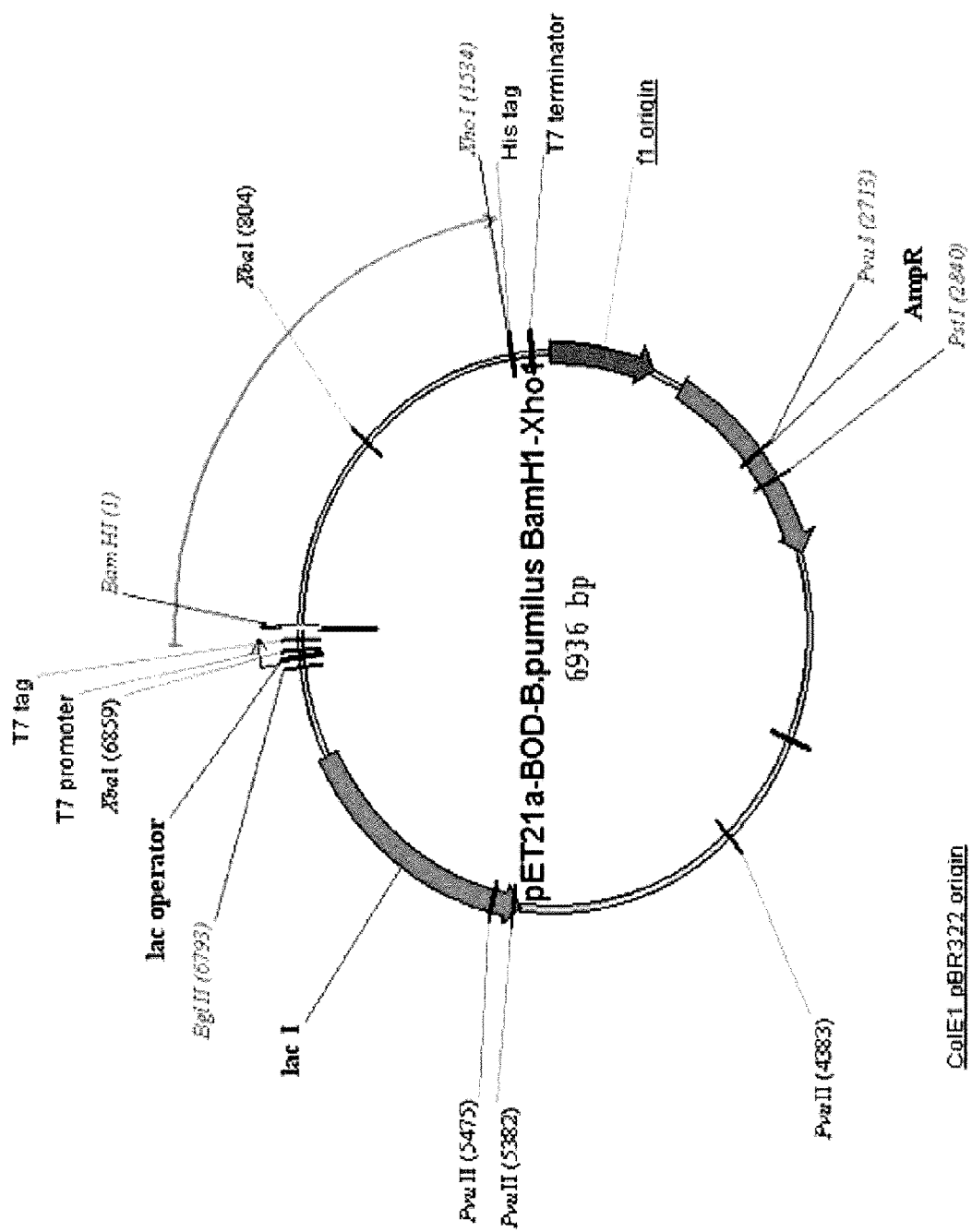
FIG. 2 represents the plasmid map of the pFD1 vector.

The plasmid map of the pFD1 vector is represented in FIG. 2.

1.3 Culture Medium

LB Rich Medium:
10 g/l tryptone
5 g/l yeast extract
5 g/l NaCl
Distilled H$_2$O qs 1 L
pH not adjusted, autoclaved for 50 min at 1 bar.

2. Genetic Engineering Techniques

2.1 Transformation of Supercompetent Bacteria

Supercompetent DH$_{5\alpha}$ bacteria are prepared using the SEM method (Simple and Efficient Method) according to the protocol described by Inoue et al. (Inoue et al. 1990, Gene 96:23-28).

2.2 DNA Preparation

A plasmid DNA purification kit (Quiagen) is used for the DNA preparations in small and large amounts.

2.3 Double-Stranded DNA Sequencing

The double-stranded DNA is sequenced. The sequencing reactions are carried out with the BigDye Terminator v1.1 or v3.1 sequencing kit. The reagent contains the 4 ddNTPs with various fluorescent labels (BigDye Terminators), the Ampli-Taq DNA polymerase, and all the other components necessary for the reaction. The extension products should be purified before being passed through an ABI 3130xl sequencer, in order to remove the unincorporated labels, the salts and the other contaminants.

2.4 Construction of the BOD Expression Vector

The PCR is carried out with the Phusion HF DNA polymerase on the genomic DNA of the *Bacillus pumilus* bacterium, strain SAFR-032. The two oligodeoxyribonucleotides, complementary to the 3' and 5' ends of the DNA sequence of the gene encoding the *Bacillus pumilus* BOD (SEQ ID No. 3 and 4) will be used as primers for the DNA synthesis.

The amplified product and also the pET21a plasmid are then treated with the two restriction enzymes BamH1 and Xho1, the recognition sequences of which have been introduced into the sense oligonucleotide for BamH1 and the antisense oligonucleotide for Xho1, respectively denoted SEQ ID No. 3 and 4. The digestion products are gel-purified with the "Nucleospin®" kit (NucleoSpin® Extract II, Clontech Laboratories, Inc.) and the BOD gene is then ligated into the plasmid by coincubation with T4 DNA ligase at 37° C. overnight. The newly formed plasmids are then selected and amplified by transformation of DH5α bacteria on a plate containing ampicillin.

TABLE II

List of primers used

| Primer name | Sequence | SEQ ID No. |
|---|---|---|
| *B.pumilus*_S_BamH1 | CATGGATCCATGAACCTA GAAAAATTTGTTGACGAG | 3 |
| *B.pumilus*_AS_Xho1 | TACCTCGAGAATAATATC CATCGGCCTCATCATGTC | 4 |

3. Production, Purification and Characterization of the *Bacillus Pumilus* Bilirubin Oxidase Enzyme 3.1 Production of Wild-Type BOD Enzymes The BOD enzyme is produced in the *E. coli* $BL_{21}$ star strain by the pET21a recombinant plasmid carrying the sequence encoding wild-type BOD. A 50 ml preculture of LB medium supplemented with ampicillin (150 mg/l) (LBA) and 0.25 mM $CuSO_4$ is inoculated with a clone isolated on an LB agar plate supplemented with ampicillin (100 mg/l), and left shaking, at 220 rpm, overnight at 37° C. Two liters of LBA medium containing 0.25 mM $CuSO_4$, in a 5 L Erlenmeyer flask, are then inoculated at $1/100^{th}$. The latter is incubated at 37° C. with shaking (220 rpm) until an $OD_{600nm}$ of between 0.8 and 1 $OD_{600nm}$/ml is obtained. The culture is then induced with 200 μM of IPTG and left shaking (180-220 rpm) at 25° C. for 4 hours. The cells are then transferred into a sterile 2 L Schott bottle containing a magnetic bar, so as to continue, for 20 hours, the culture and the protein induction with shaking under anaerobic conditions in order to increase the incorporation of copper into the bacteria. The cells harvested by centrifugation (4000 g, 4° C.) are washed in water and stored at −20° C.

It is important to emphasize that the induction of the expression of this BOD in the *E. coli* bacterium is carried out in only 24 hours; this represents a considerable advantage compared with the protocols for induction of the commercial enzymes currently available. This is because the production of BODs derived from *Myrothecium verrucaria* can require induction periods of up to 5 days.

3.2 Purification of Wild-Type BOD Enzymes 3.2.1 Rupture of Cells and Treatment with DNase I The cell pellet, derived from two liters of culture, is taken up in 40 ml of 50 mM sodium phosphate buffer containing 500 mM NaCl and 20 mM imidazole, pH 7.6, and sonicated 10 times at a sonication power of 40 W for 3 minutes by cycle of a second of ultrasound and a second of interruption. The sample obtained, called crude extract, is supplemented with a final concentration of 2 mM of $MgCl_2$ and treated for 30 minutes at ambient temperature with DNase I (1 U/ml of crude extract). The insoluble cell debris is then removed from the crude extract by centrifugation for 60 minutes at 20 000 g.

3.2.2 Affinity Chromatography on Nickel Column

The sonication supernatant filtered through a 0.22 μm filter and diluted to an $OD_{280nm}$ of 10 is injected onto a HisPrep FF 16/10 affinity column (GC Healthcare®), coupled to the AKTA purifier system (GC Healthcare®), equilibrated in a 50 mM sodium phosphate buffer containing 500 mM NaCl and 20 mM imidazole, pH 7.6. The elution is carried out with a gradient of 5% to 30% of a 50 mM sodium phosphate buffer containing 500 mM NaCl and 1M imidazole, pH 7.6, at a flow rate of 1 ml/min. The fractions containing the BOD protein are identified by means of an ABTS activity test and are combined, concentrated and desalified with a 50 mM sodium phosphate buffer, pH 7.6, by centrifugation on an Amicon YM10 membrane. At this stage, the BOD protein is pure and can be stored at −20° C. in soluble form.

Here again, by comparing with the commercially available BOD purification methods, the clear advantage resulting from the use of this protein can be emphasized. This is because a single purification step is necessary in order to obtain a pure enzyme, as opposed to the succession of chromatographies (size exclusion, anion or cation exchange, hydrophobic, etc.) essential for the commercial BODs.

3.2.3 Characterization of Wild-Type BOD Enzymes 3.2.3.1 Molecular Weight Determination The analysis of the weight of the whole protein was carried out on the LCQ Deca XP mass spectrometer coupled upstream of a nano liquid chromatography apparatus fitted with a C4 desalting and pre-concentrating column (μ-Precolumn™ Cartridge; Acclaim PepMap 300; internal Ø 300 μm×5m; LC Packings Dionex) and of a C4 analytical column (C4 PepMap 300; internal Ø 75 μm×5 cm; LC Packings Dionex).

A weight of 61005.91 Da was obtained for the BOD, i.e. a difference of 130.4 Da compared with the theoretical weight of the protein; the theoretical weight is calculated for the protein truncated at the N-terminal methionine, a difference of only 0.80 Da is found, which demonstrates cleavage of this amino acid in the bacterium during the protein maturation process.

3.2.3.2 Concentration Measurement

The enzyme concentration of a solution is calculated according to the Bradford technique using BSA as standard (Bradford, anal. *Biochimie* 72:248, 1976).

3.2.3.3 Enzymatic Assay

The enzymatic assays are carried out using a Varian spectrophotometer in a 0.1M citrate/phosphate buffer at 37° C. in a volume of 3 ml, with the oxidation of ABTS being followed at 420 nm as a function of time ($\epsilon_{420nm}$=36 mM$^{-1}$ cm$^{-1}$). The specific activity of the enzyme is expressed in µmol of ABTS oxidized per minute and per mg of protein. The standard ABTS concentration used is 1 mM. The enzyme is diluted so as to measure a slope between 0.05 and 0.3 OD$_{420nm}$/min.

4. Techniques for Studying the Enzymatic Properties of the Wild-Type *Bacillus pumilus* BOD Enzyme

4.1 Determination of the Kinetic ($k_{cat}$) and Michaelis ($K_M$) Constants in the Stationary State

4.1.1 the Substrate is 2,2'-azinobis(3-ethylbenzothiazoline-6-sulphonic acid) (ABTS)

The experiments are carried out at 37° C. on a Varian spectrophotometer in a 0.1 M citrate/phosphate buffer, pH 3. The ABTS concentration varies in the test from 0 to 5 mM. The test is triggered by adding enzyme. The experimental points are analysed by nonlinear regression according to the Michaelis-Menten model using the Sigma-plot 6.0 software according to the equation below:

Michaelis-Menten model: $k_{ss}=k_{cat}*[S]/(K_M+[S])$

Results:
$k_{cat}$=391.3 s$^{-1}$ and $K_M$=31.7 µM.

Figure 3:
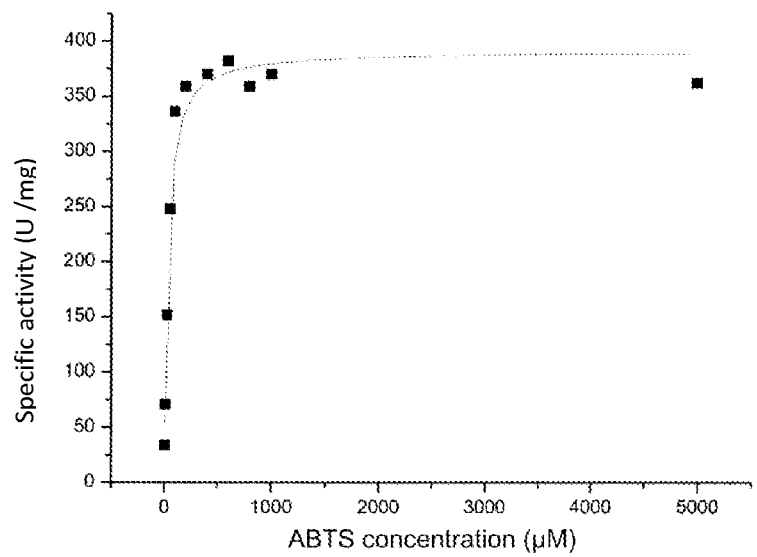
FIG. 3 is a graph illustrating the specific activity, in U/mg, of the *Bacillus pumilus* BOD as a function of the ABTS concentration at 37° C.

FIG. 3 illustrates graphically the specific activity, in U/mg, of the *Bacillus pumilus* BOD as a function of ABTS concentration. By way of comparison, the homologous CotA protein of *Bacillus subtilis* exhibits, with respect to ABTS under the same optimal activity conditions, a $k_{cat}$ of 322 s$^{-1}$ for a $K_M$ of 124 µM (Martins et al., 2008. *J Biol Inorg Chem*, 13:183-193).

4.1.2 The Substrate is Unconjugated Bilirubin

The experiments are carried out at 37° C. in a Varian spectrophotometer in a 50 mM sodium phosphate buffer, pH 7. The bilirubin concentration varies in the test from 0 to 60 µM. The test, triggered by the addition of enzyme, consists in following the oxidation of the bilirubin at 450 nm by colorimetric change ($\epsilon_{450nm}$=32 mM$^{-1}$ cm$^{-1}$). The experimental points are analysed by nonlinear regression according to the Michaelis-Menten model using the Sigma-plot 6.0 software according to the equation below:

Michaelis-Menten model: $k_{ss}=k_{cat}*[S]/(K_M+[S])$

Results:
$k_{cat}$=70 s$^{-1}$ and $K_M$=22 µM.

Figure 4:
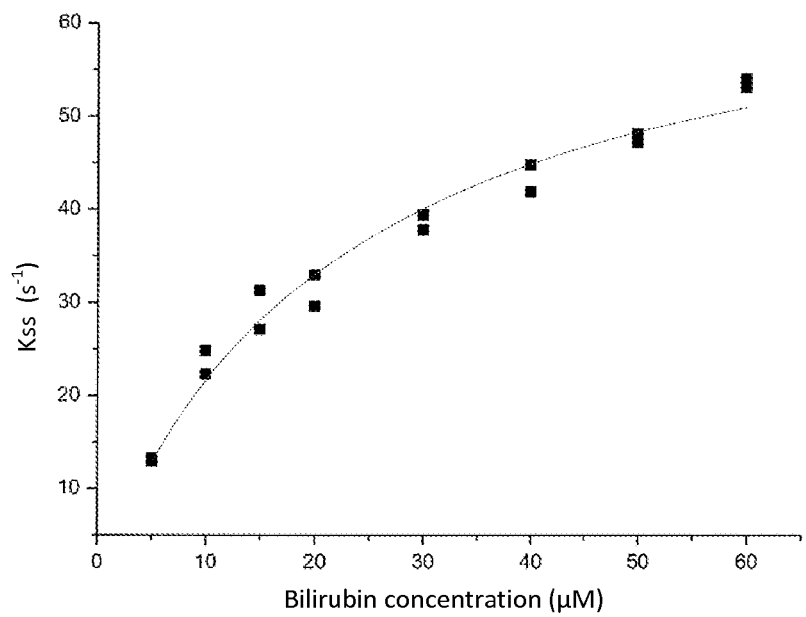
FIG. 4 is a graphic representation of the Michaelis-Menten equation ($k_{ss}$ in $s^{-1}$ as a function of the unconjugated bilirubin concentration) for the *Bacillus pumilus* BOD at 37° C.

FIG. 4 is the graphic representation of the Michaelis-Menten equation ($k_{ss}$ in s$^{-1}$ as a function of unconjugated bilirubin concentration) for the *Bacillus pumilus* BOD.

4.1.3 The Substrate is Conjugated Bilirubin

The experiments are carried out at 37° C. on a Varian spectrophotometer in a 50 mM sodium phosphate buffer, pH 4.8. The bilirubin concentration varies in the test from 0 to 150 µM. The test, triggered by adding enzyme, consists in following the oxidation of the conjugated bilirubin at 440 nm by colorimetric change ($\epsilon_{440nm}$=25 mM$^{-1}$ cm$^{-1}$). The experimental points are analysed by nonlinear regression according to the Michaelis-Menten model using the Sigma-plot 6.0 software according to the equation below:

Michaelis-Menten model: $k_{ss}=k_{cat}*[S]/(K_M+[S])$

Results:
$k_{cat}$=66.8 s$^{-1}$ and $K_M$=35.1 µM.

Figure 5:
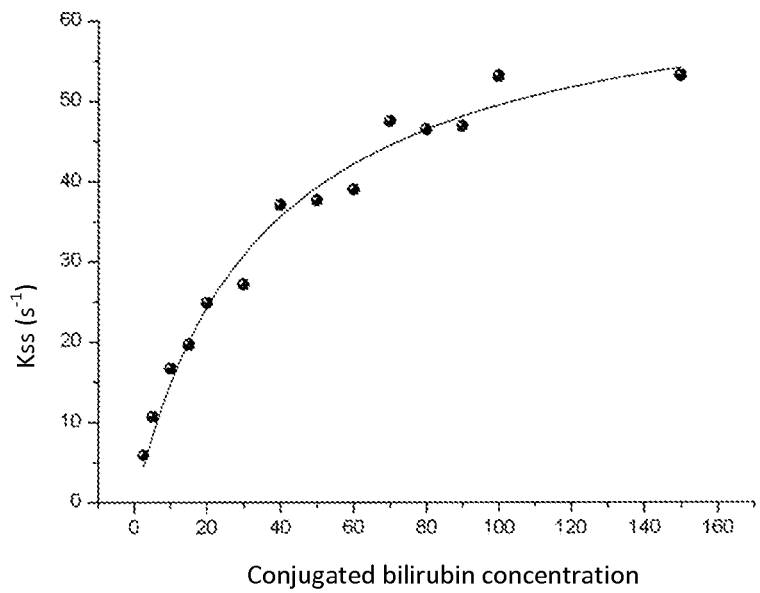
FIG. 5 represents the catalytic activity for oxidation of conjugated bilirubin by the *Bacillus pumilus* BOD at 37° C. in a 50 mM citrate/phosphate buffer, pH 4.8.

FIG. 5 represents the catalytic activity for oxidation of the conjugated bilirubin by the *Bacillus pumilus* BOD at 37° C. in a 50 mM citrate/phosphate buffer, pH 4.8.

4.1.4 The Substrate is Syringaldazine (SGZ)

The experiments are carried out at 37° C. on a Varian spectrophotometer in a 50 mM citrate/phosphate buffer, pH 6.2. The SGZ concentration, diluted in methanol, varies in the test from 0 to 300 µM. The test, triggered by adding the enzyme, consists in following the oxidation of the SGZ at 530 nm by coloroimetric change ($\epsilon_{530nm}$=64 mM$^{-1}$ cm$^{-1}$). The experimental points are analysed by nonlinear regression according to the Michaelis-Menten model with competitive inhibition, using the Sigma-plot 6.0 software according to the equation below:

Michaelis-Menten model with competitive inhibition:

$k_{ss}=k_{cat}*[S]/(K_M+[S]+[S]^2/K_i)$

Results:
$k_{cat}$=116.1; $K_M$=45.6 µM and $K_i$=82.9 µM.

Figure 6:
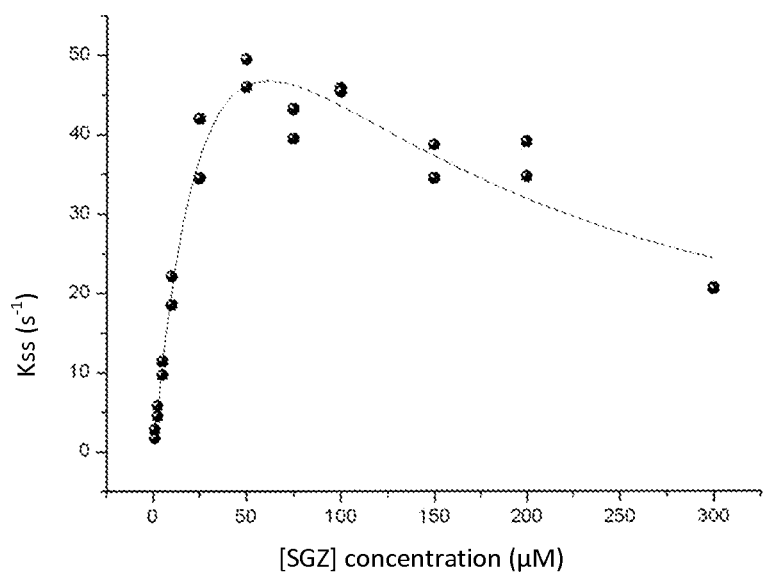
FIG. 6 represents the catalytic activity for oxidation of syringaldazine (SGZ) by the *Bacillus pumilus* BOD at 37° C. in a 50 mM citrate/phosphate buffer, pH 6.2.

FIG. 6 represents the catalytic activity for oxidation of syringaldazine by the *Bacillus pumilus* BOD at 37° C. in a 50 mM citrate/phosphate buffer, pH 6.2.

4.1.5 The Substrate is 2,6-Dimethoxyphenol (DMP)

The experiments are carried out at 37° C. on a Varian spectrophotometer in a 50 mM sodium phosphate buffer, pH 6.8. The 2,6-dimethoxyphenol concentration varies in the test from 0 to 4000 µM. The test, triggered by adding the enzyme, consists in following the oxidation of the DMP at 468 nm by coloroimetric change ($\epsilon_{468nm}$=14.8 mM$^{-1}$ cm$^{-1}$). The experimental points are analysed by nonlinear regression according to the Michaelis-Menten model using the Sigma-plot 6.0 software according to the equation below:

Michaelis-Menten model: $k_{ss}=k_{cat}*[S]/(K_M+[S])$

Results:
$k_{ss}$=57.3 s$^{-1}$ and $K_M$=822 µM.

Figure 7:
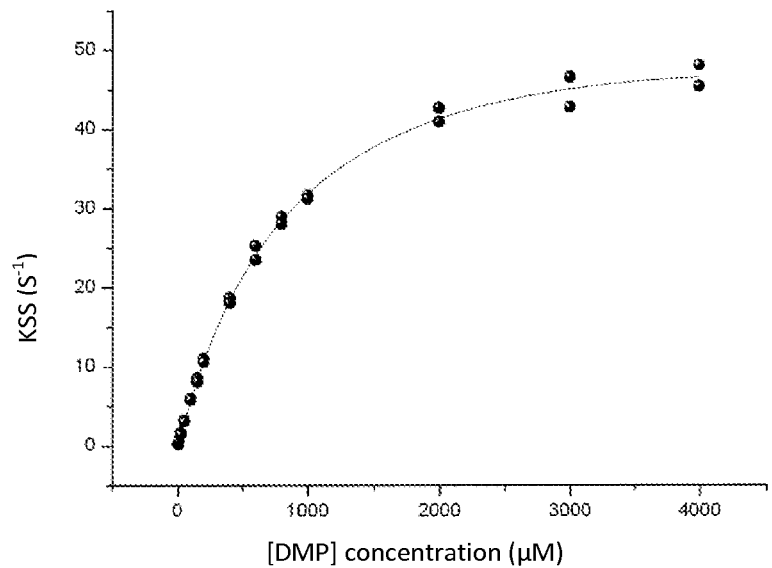
FIG. 7 represents the catalytic activity for oxidation of DMP by the *Bacillus pumilus* BOD at 37° C. in a 50 mM citrate/phosphate buffer, pH 6.8.

FIG. 7 represents the catalytic activity for oxidation of DMP by the *Bacillus pumilus* BOD at 37° C. in a 50 mM citrate/phosphate buffer, pH 6.8.

4.2 Study as a Function of pH

4.2.1 Activity as a Function of pH

4.2.1.1 ABTS

The study of the variation in the reaction rate constant as a function of pH is carried out on a pH range of from 3 to 7 in a 0.1 M citrate/phosphate buffer, using 1 mM ABTS as substrate. The experiments are carried out at 37° C. using a Varian spectrophotometer. The activity is followed by oxidation of the ABTS resulting in a colorimetric change measured at 420 nm. The test is triggered by adding enzyme.

Figure 8:
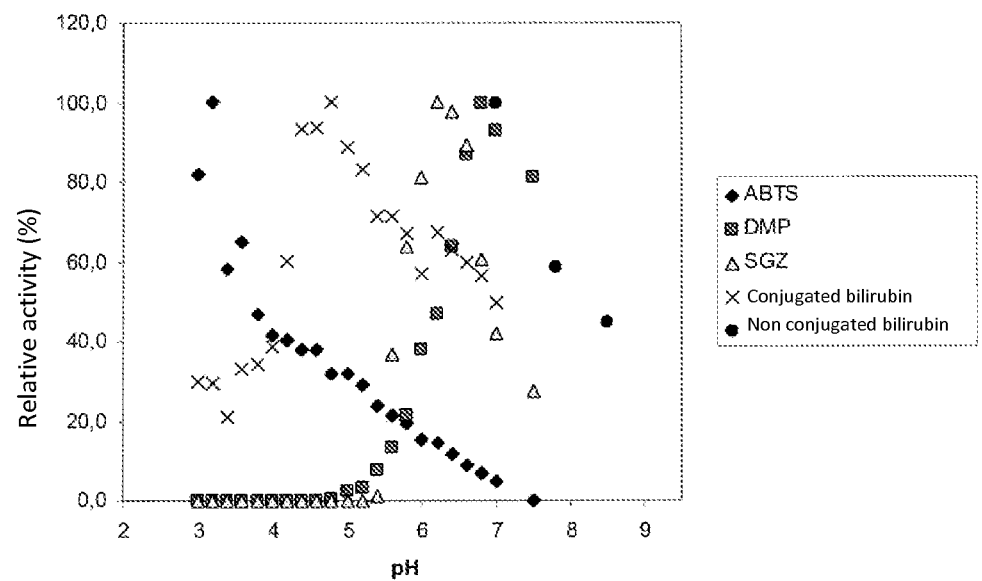
FIG. 8 represents the relative activity of the *Bacillus pumilus* BOD with respect to various substrates as a function of the pH.

The results of the oxidation of ABTS, as a function of pH, by the *Bacillus pumilus* BOD are represented as relative activity on the graph of FIG. 8.

4.2.1.2 Unconjugated Bilirubin

The study of the variation in the reaction rate constant as a function of pH is carried out on a pH range of from 7 to 8.5 in a 0.2 M tris-HCl buffer, using 30 µM unconjugated bilirubin as substrate. The experiments are carried out at 37° C. using a Varian spectrophotometer. The activity is followed by oxidation of the bilirubin resulting in a colorimetric change measured at 450 nm ($\epsilon_{450nm}$=32 mM$^{-1}$ cm$^{-1}$). The test is triggered by adding enzyme.

The results of the oxidation of unconjugated bilirubin, as a function of pH, by the *Bacillus pumilus* BOD are represented as relative activity on the graph of FIG. 8.

4.2.1.3 Conjugated Bilirubin

The study of the variation in the reaction rate constant as a function of pH is carried out on a pH range of from 3 to 7 in a 0.1 M citrate/phosphate buffer, using 100 µM conjugated bilirubin as substrate. The experiments are carried out at 37° C. using a Varian spectrophotometer. The activity is followed by oxidation of the conjugated bilirubin resulting in a colorimetric change measured at 440 nm. The test is triggered by adding enzyme.

The results of the oxidation of conjugated bilirubin, as a function of pH, by the *Bacillus pumilus* BOD are represented as relative activity on the graph of FIG. 8.

4.2.1.4 Syringaldazine (SGZ)

The study of the variation in the reaction rate constant as a function of pH is carried out on a pH range of from 3 to 7.5 in a 0.1 M citrate/phosphate buffer, using 22 µM syringaldazine as substrate. The experiments are carried out at 37° C. using a Varian spectrophotometer. The activity is followed by oxidation of the syringaldazine resulting in a colorimetric change measured at 530 nm. The test is triggered by adding enzyme.

The results of the oxidation of syringaldazine, as a function of pH, by the *Bacillus pumilus* BOD are represented as relative activity on the graph of FIG. 8.

4.2.1.5 2,6-Dimethoxyphenol (DMP)

The study of the variation in the reaction rate constant as a function of pH is carried out on a pH range of from 3 to 7.5 in a 0.1 M citrate/phosphate buffer, using 1 mM DMP as substrate. The experiments are carried out at 37° C. using a Varian spectrophotometer. The activity is followed by oxidation of the DMP resulting in a colorimetric change measured at 468 nm. The test is triggered by adding enzyme.

The results of the oxidation of DMP, as a function of pH, by the *Bacillus pumilus* BOD are represented as relative activity on the graph of FIG. 8.

4.2.2 Stability as a Function of pH

The stability as a function of pH, of the wild-type BOD, is determined by dilution of the enzyme, purified to homogeneity, in a mixed buffer ranging from pH 3 to 9 at ambient temperature. This mixed buffer is composed of 120 mM Tris, 30 mM imidazole and 30 mM acetic acid, the ionic strength of which is adjusted to 190 mM with NaCl. Various samples are taken as a function of time. The residual activity is measured at 4° C. using a Varian spectrophotometer, in a 0.1 M citrate/phosphate buffer, pH 3, containing 1 mM ABTS.

Figure 9A:
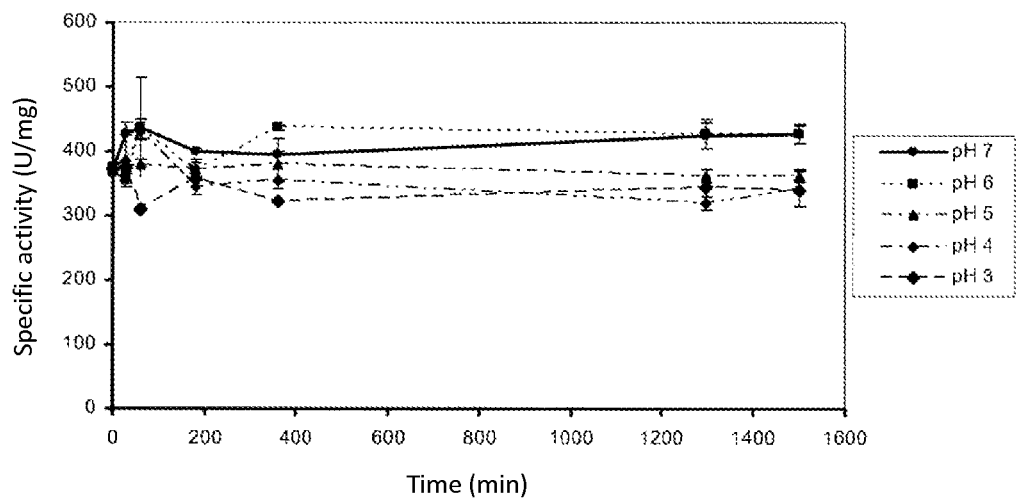
FIGS. 9A and 9B are graphs representing the stability as a function of pH of the *Bacillus pumilus* BOD on ABTS oxidation at 4° C.
Figure 9B:
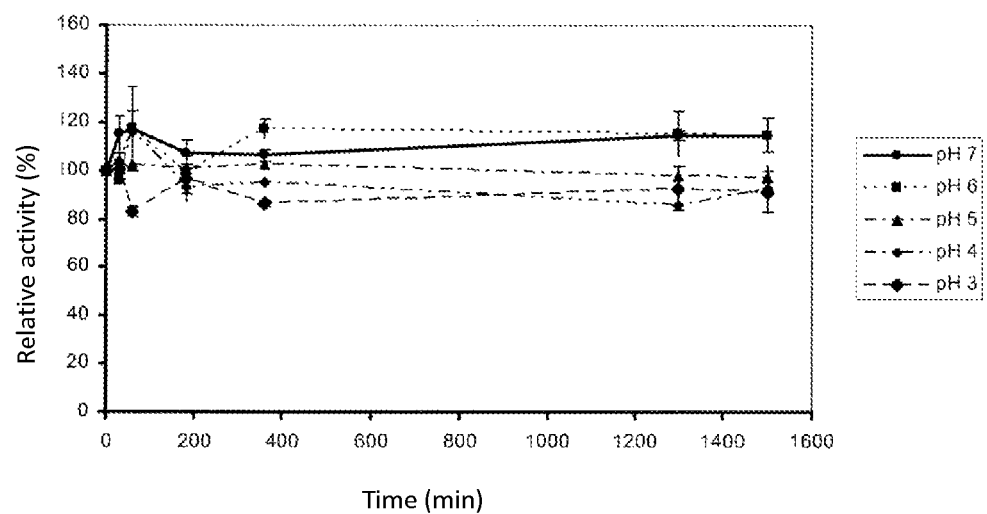

The results of specific activity and of relative activity of the oxidation of ABTS as a function of pH at 4° C. are represented in the graphs of FIGS. 9A and 9B.

4.3 Study as a Function of the Temperature

4.3.1 Activity as a Function of Temperature

The study of the variation in the reaction rate constant as a function of temperature is carried out in a 0.1 M citrate/phosphate buffer, pH 3, in the presence of 1 mM of ABTS. The temperature ranges from 10 to 85° C. The activity is followed on a temperature-regulated Varian Cary UV Biomelt spectrophotometer. The test is triggered by adding enzyme.

Figure 10:
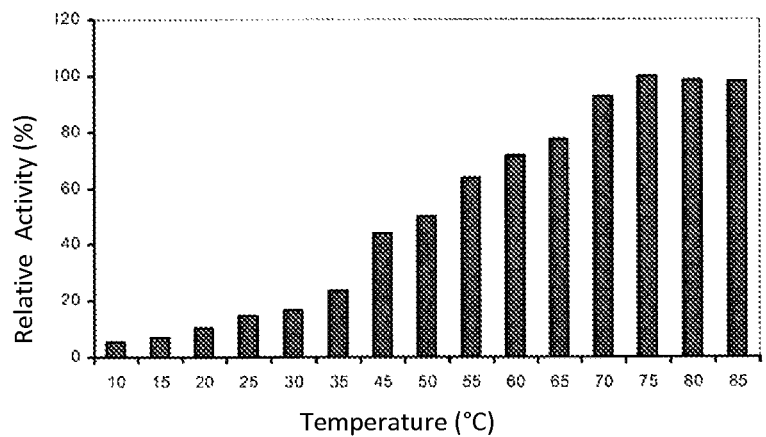
FIG. 10 is a histogram representing ABTS oxidation as relative activity by the *Bacillus pumilus* BOD as a function of temperature.

FIG. 10 is a histogram representing the relative activity of the *Bacillus pumilus* BOD as a function of temperature on ABTS oxidation.

4.3.2 Stability of the Enzyme as a Function of Temperature

The enzyme is preincubated at a concentration of 10 mg/ml in a dry bath at 80° C. 2 µl samples are taken and the enzyme is diluted in a 50 mM sodium phosphate buffer, pH 7.6, so as to adjust the enzyme concentration for the activity test. The residual activity of the enzyme incubated at 80° C. is determined using a Varian spectrophotometer, in a 0.1 M citrate/phosphate buffer, pH 3, at 37° C., in the presence of 1 mM of ABTS. The test is triggered by adding enzyme.

Figure 11A:
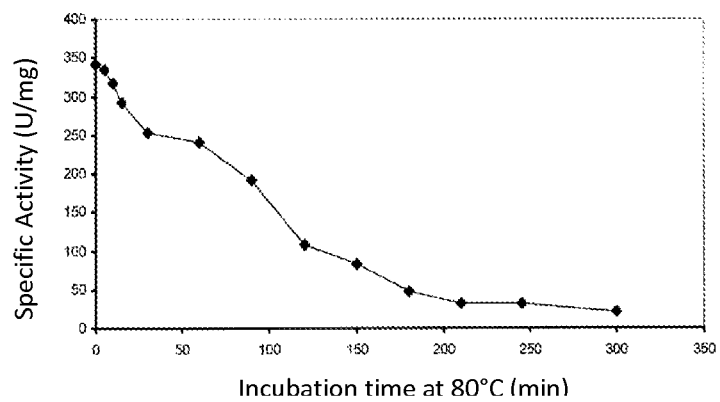
FIGS. 11A and 11B represent graphically the stability (expressed as specific activity and as relative activity on ABTS oxidation) of the *Bacillus pumilus* BOD as a function of enzyme incubation time at 80° C.
Figure 11B:
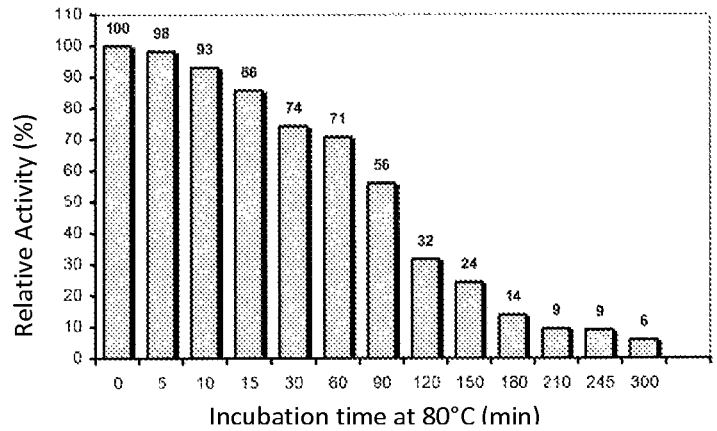

FIGS. 11A and 11B represent graphically the stability (expressed as specific activity and as relative activity on ABTS oxidation) of the *Bacillus pumilus* BOD as a function of enzyme incubation time at 80° C.

4.4 Study of the Activity as a Function of the Presence of Urea

Figure 12A:
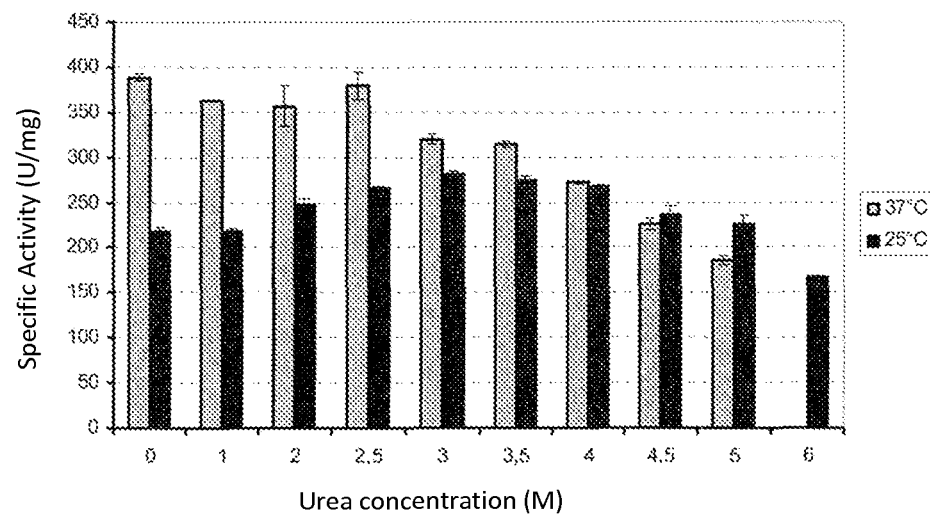
FIGS. 12A and 12B represent graphically the activity (expressed as specific activity and as relative activity on ABTS oxidation) of the *Bacillus pumilus* BOD as a function of urea concentration at 25° C. or 37° C. in a 100 mM citrate/phosphate buffer, pH 3.
Figure 12B:
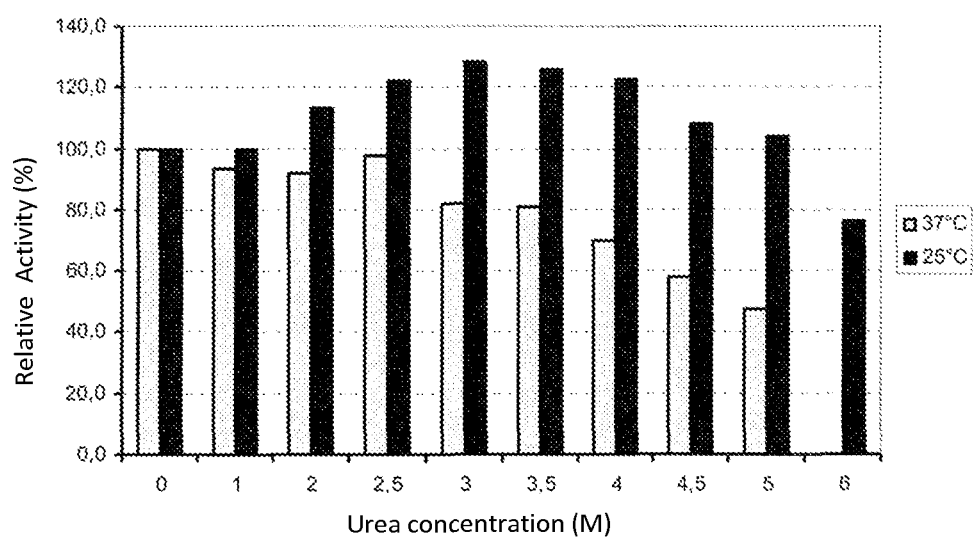

The protocol described above in point 4.1.1 was reproduced in the presence of a urea concentration ranging between 0 and 6 M. FIGS. 12A and 12B represent graphically the activity (expressed as specific activity and as relative activity on ABTS oxidation) of the *Bacillus pumilus* BOD as a function of urea concentration at 25° C. and at 37° C.

At 25° C., an activating effect of the urea on the BOD is clearly observed. This effect could be due to a slight conformational modification of the active site of the enzyme that would be responsible for better enzymatic efficiency; this phenomenon, which is known, has already been described for other proteins (see Hong-Jie Zhang et al. Biochemical and Biophysical Research Communications 238, 382-386 (1997) and Fan et al. Biochem. J. (1996) 315, 97-102).

At 37° C., this effect is not found. It is possible to put forward the hypothesis that the combined effect of the temperature and of the urea results in too great a modification of the active site, consequently leading to a decrease in the performance levels of the enzyme.

4.5 Study of the Activity as a Function of the Presence of NaCl

The experiments are carried out at 37° C. on a Varian spectrophotometer in a 50 mM citrate/phosphate buffer, pH 6.2, with increasing concentrations of NaCl, from 0 mM to 1000 mM. The concentration of SGZ, diluted in methanol, is fixed in the test at 50 µM. The test, triggered by adding enzyme, consists in following the oxidation of the SGZ at 530 nm by colorimetric change ($\epsilon_{530nm}$=64 mM$^{-1}$. cm$^{-1}$).

Figure 13:
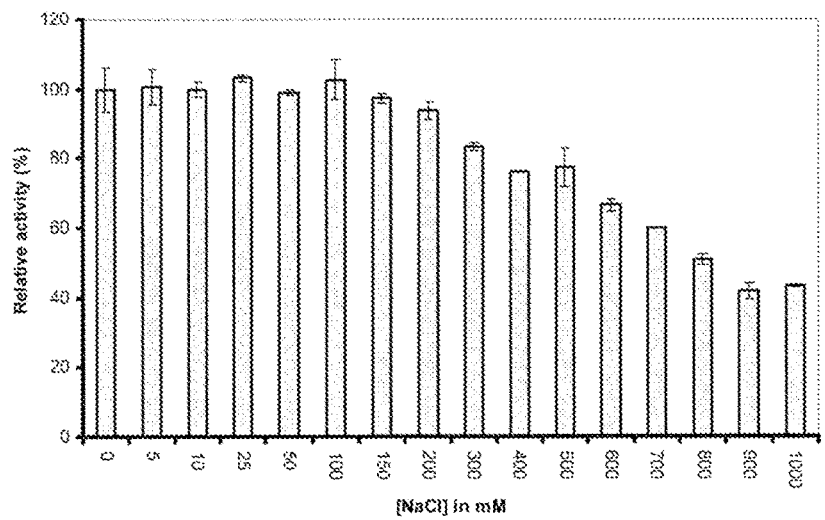
FIG. 13 represents the relative activity of the oxidation of SGZ by the *Bacillus pumilus* BOD as a function of NaCl concentration.
Figure 14:
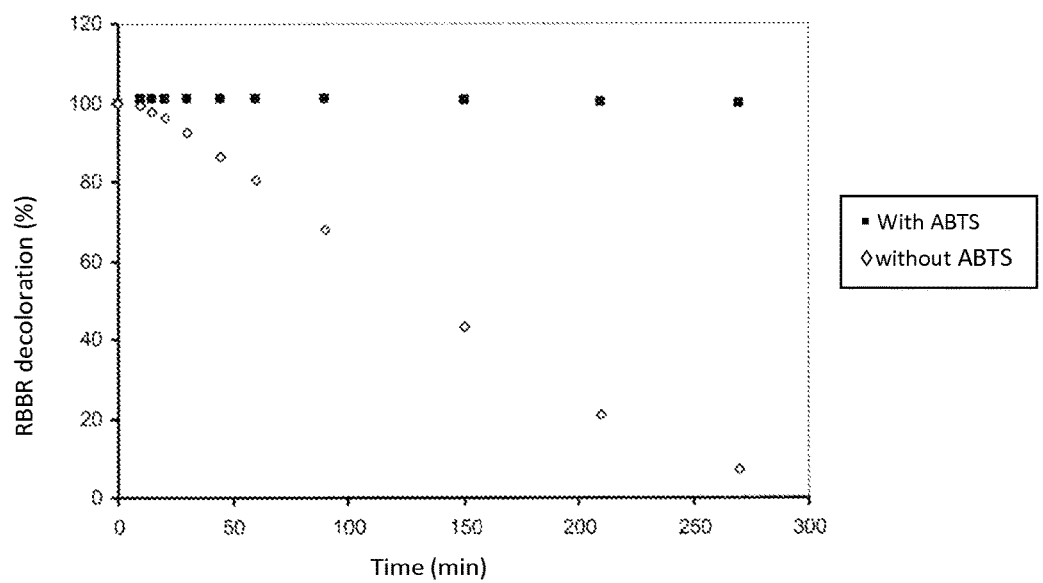
FIG. 14 represents the discoloration of RBBR at 80 mg.l$^{-1}$ by the *Bacillus pumilus* BOD at 37° C. in a 50 mM potassium phosphate buffer, pH 6, in the presence or absence of 10 μM ABTS.

FIG. 13 represents the relative activity of SGZ oxidation by the *Bacillus pumilus* BOD as a function of NaCl concentration.

4.6 Study of the Activity as a Function of the Presence of DTT or of EDTA

The experiments are carried out at 37° C. on a Varian spectrophotometer in a 50 mM citrate/phosphate buffer, pH 6.2, with increasing concentrations of DTT, from 0 mM to 50 µM, or else of EDTA, from 0 to 125 mM. The concentration of SGZ, diluted in methanol, is fixed in the test at 50 µM. The test, triggered by adding enzyme, consists in following the oxidation of the SGZ at 530 nm by colorimetric change ($\epsilon_{530nm}$=64 mM$^{-1}$.cm$^{-1}$). Table III below collates the results obtained, presented in relative activity form.

TABLE III

| Compound | Concentration (mM) | Relative activity (%) |
| --- | --- | --- |
| EDTA | 0 | 100 ± 0 |
|  | 0.1 | 97 ± 1 |
|  | 1 | 99 ± 5 |
|  | 10 | 95 ± 1 |
|  | 25 | 98 ± 3 |
|  | 50 | 99 ± 4 |
|  | 75 | 95 ± 2 |
|  | 100 | 95 ± 1 |
|  | 125 | 89 ± 3 |
| DTT | 0 | 100 ± 0 |
|  | 0.001 | 99 ± 4 |
|  | 0.005 | 93 ± 2 |
|  | 0.01 | 93 ± 4 |
|  | 0.015 | 94 ± 3 |
|  | 0.03 | 85 ± 1 |
|  | 0.05 | 81 ± 4 |

4.7 Study of the Remazol Brilliant Blue R (RBBB) Discoloration Activity

Like many other laccases and bilirubin oxidases, the *Bacillus pumilus* BOD has a discolouring activity on dyes used in the textile industry. Remazol Brilliant Blue R(RBBR) was selected as an example, and the discoloration thereof is measured over time in the presence or absence of a mediator such as ABTS.

The experiments are carried out at 37° C. on a Varian spectrophotometer, in a 50 mM potassium phosphate buffer, pH 6, in the absence or presence of ABTS at 3 ml. The RBBR concentration is fixed at 80 mg.l$^{-1}$ in each tank. The test, triggered by adding 10 µg of enzyme, consists in following, over time, the discoloration of the RBBR dye at 593 nm.

FIG. 13 represents the discoloration of RBBR by the *Bacillus pumilus* BOD at 3.33 µg.ml$^{-1}$ at 37° C. in a 50 mM potassium phosphate buffer, pH 6, in the absence or presence of ABTS at 10 µM.

5. Verification of the Presence of the Four Coppers of the *Bacillus pumilus* Bilirubin Oxidase The presence of the 4 coppers is determined by means of a bioquinoline assay using a calibration range for copper concentration in order to measure the molar concentration of copper (Felsenfeld, G. 1960. Arch. Biochem. Biophys., 87, 247-251; Griffiths et al. 1961, J. Biol. Chem., 236, 1850-1856); the results are given in Table III.

Each measurement, based on a colorimetric assay at 546 nm, is carried out in duplicate.

This techniques makes it possible to show the presence of 15.3 µM of copper for a BOD protein sample at 3.75 µM, i.e. a ratio of 4.08, and clearly confirms the presence of the four copper ions associated with the enzyme.

Finally, in order to confirm the presence of the 4 coppers in the BOD protein, an elemental analysis on the coppers of the protein was carried out by atomic absorption. The results clearly confirmed the presence of 4 coppers per protein.

TABLE IV

Experimental protocol for the bioquinoline assay necessary for assaying the copper of the BOD.

| Sample | Copper solution (solution 2) (µl) | Imidazole buffer (solution 1) (µl) | Biquinoline solution (3) (µl) | Total volume (µl) | Copper concentration in the sample (µM) |
| --- | --- | --- | --- | --- | --- |
| 1 | 0 | 1200 | 1800 | 3000 | 0 |
| 2 | 0 | 1200 | 1800 | 3000 | 0 |
| 3 | 120 | 1080 | 1800 | 3000 | 12.59 |
| 4 | 120 | 1080 | 1800 | 3000 | 12.59 |
| 5 | 240 | 960 | 1800 | 3000 | 25.18 |
| 6 | 240 | 960 | 1800 | 3000 | 25.18 |
| 7 | 360 | 840 | 1800 | 3000 | 37.77 |
| 8 | 360 | 840 | 1800 | 3000 | 37.77 |
| 9 | 480 | 720 | 1800 | 3000 | 50.36 |
| 10 | 480 | 720 | 1800 | 3000 | 50.36 |
| 11 | 600 | 600 | 1800 | 3000 | 62.95 |
| 12 | 600 | 600 | 1800 | 3000 | 62.95 |
| BOD_1 (3.75 µM) | 450 | 750 | 1800 | 3000 | 15.7 |
| BOD_2 (3.75 µM) | 450 | 750 | 1800 | 3000 | 15.3 |

What is claimed is:

1. A BOD electrode comprising a conductive material coated with a deposit comprising at least one bilirubin oxidase (BOD), wherein said BOD has a percentage identity of at least 97% with respect to the BOD of *Bacillus pumilus* of SEQ ID No. 2, and it is bound to four copper atoms.

2. The BOD electrode of claim 1 wherein said BOD is the BOD of *Bacillus pumilus* of SEQ ID No. 2.

3. The BOD electrode of claim 1 wherein said conductive material is selected in the group consisting of platinum, copper, silver, aluminium, gold, steel or carbon.

4. The BOD electrode of claim 1 wherein said deposit comprising at least one purified BOD also comprises a redox polymer.

5. The BOD electrode of claim 1 wherein said electrode is coated with a membrane which prevents the detachment of said BOD from said electrode.

6. Method for measuring the bilirubin concentration in solution in a liquid sample, comprising the following steps:
   a) measuring the absorbance at λmax=440 nm of said liquid sample before enzymatic reaction;
   b) introducing into said liquid sample the BOD electrode according to claim 1;
   c) measuring the absorbance at λmax=440 nm of said liquid sample after enzymatic reaction;
   d) calculating the difference in absorbances measured in steps a) and c) and comparing with differences in absorbances measured for standard solutions having a known bilirubin content; and
   e) determining the bilirubin concentration of said liquid sample.

7. Method for degrading the bilirubin present in a sample comprising introducing into said liquid sample the BOD electrode according to claim 1.

8. Method for oxidizing dyeing of keratin fibers comprising contacting into said keratin fibers the BOD electrode according to claim 1.

9. Method for treating wood pulp comprising contacting said wood pulp with the BOD electrode according to claim 1.

10. Method for discoloring dyes used in industrial media comprising contacting said industrial media with the BOD electrode according to claim 1.

11. Bilirubin biosensor, characterized in that it is constituted of an electrode according to claim 1.

12. Oxygen sensor, characterized in that it is constituted of an electrode according to claim 1.

13. Enzymatic biofuel cell comprising an anode on which an enzyme catalyzing an oxidation reaction is immobilized and an electrode according to claim 1 as cathode.

* * * * *

SEQUENCE LISTING

<160> NUMBER OF SEQ ID NOS: 6

<210> SEQ ID NO 1
<211> LENGTH: 1593
<212> TYPE: DNA
<213> ORGANISM: Bacillus pumilus

```
<220> FEATURE:
<221> NAME/KEY: CDS
<222> LOCATION: (1)..(1593)

<400> SEQUENCE: 1
```

| | | | | | | | | | | | | | | | | |
|---|---|---|---|---|---|---|---|---|---|---|---|---|---|---|---|---|
| atg | gct | agc | atg | act | ggt | gga | cag | caa | atg | ggt | cgc | gga | tcc | atg | aac | 48 |
| Met | Ala | Ser | Met | Thr | Gly | Gly | Gln | Gln | Met | Gly | Arg | Gly | Ser | Met | Asn | |
| 1 | | | | 5 | | | | | 10 | | | | | 15 | | |
| cta | gaa | aaa | ttt | gtt | gac | gag | ctg | cca | att | cca | gaa | gtt | gcg | gag | ccc | 96 |
| Leu | Glu | Lys | Phe | Val | Asp | Glu | Leu | Pro | Ile | Pro | Glu | Val | Ala | Glu | Pro | |
| | | | 20 | | | | | 25 | | | | | 30 | | | |
| gtc | aaa | aag | aac | cca | aga | caa | aca | tat | tat | gaa | atc | gct | atg | gag | gag | 144 |
| Val | Lys | Lys | Asn | Pro | Arg | Gln | Thr | Tyr | Tyr | Glu | Ile | Ala | Met | Glu | Glu | |
| | 35 | | | | | 40 | | | | | 45 | | | | | |
| gta | ttt | cta | aaa | gtt | cat | aga | gac | ctg | ccc | cca | acc | aaa | cta | tgg | acc | 192 |
| Val | Phe | Leu | Lys | Val | His | Arg | Asp | Leu | Pro | Pro | Thr | Lys | Leu | Trp | Thr | |
| 50 | | | | | 55 | | | | | 60 | | | | | | |
| tat | aat | ggc | agt | ttg | cct | ggt | cca | acc | att | cat | gca | aat | cga | aat | gaa | 240 |
| Tyr | Asn | Gly | Ser | Leu | Pro | Gly | Pro | Thr | Ile | His | Ala | Asn | Arg | Asn | Glu | |
| 65 | | | | 70 | | | | | 75 | | | | | 80 | | |
| aaa | gtt | aaa | gtg | aaa | tgg | atg | aac | aaa | ttg | cca | ctt | aaa | cat | ttt | cta | 288 |
| Lys | Val | Lys | Val | Lys | Trp | Met | Asn | Lys | Leu | Pro | Leu | Lys | His | Phe | Leu | |
| | | | | 85 | | | | | 90 | | | | | 95 | | |
| ccg | gtc | gat | cac | acg | att | cac | gaa | ggc | cat | cat | gat | gaa | cca | gaa | gtc | 336 |
| Pro | Val | Asp | His | Thr | Ile | His | Glu | Gly | His | His | Asp | Glu | Pro | Glu | Val | |
| | | | 100 | | | | | 105 | | | | | 110 | | | |
| aag | acc | gtc | gtt | cat | tta | cat | ggc | ggc | gtc | aca | cca | gca | agc | agt | gac | 384 |
| Lys | Thr | Val | Val | His | Leu | His | Gly | Gly | Val | Thr | Pro | Ala | Ser | Ser | Asp | |
| | | | 115 | | | | | 120 | | | | | 125 | | | |
| ggc | tat | cca | gag | gct | tgg | ttt | tca | cga | gac | ttt | gaa | gca | acc | ggc | ccc | 432 |
| Gly | Tyr | Pro | Glu | Ala | Trp | Phe | Ser | Arg | Asp | Phe | Glu | Ala | Thr | Gly | Pro | |
| | 130 | | | | | 135 | | | | | 140 | | | | | |
| ttc | ttt | gaa | cgg | gaa | gtg | tac | gaa | tac | cca | aat | cat | cag | caa | gcc | tgc | 480 |
| Phe | Phe | Glu | Arg | Glu | Val | Tyr | Glu | Tyr | Pro | Asn | His | Gln | Gln | Ala | Cys | |
| 145 | | | | | 150 | | | | | 155 | | | | | 160 | |
| aca | ttg | tgg | tat | cac | gat | cat | gcg | atg | gca | ttg | aca | cga | tta | aat | gtg | 528 |
| Thr | Leu | Trp | Tyr | His | Asp | His | Ala | Met | Ala | Leu | Thr | Arg | Leu | Asn | Val | |
| | | | | 165 | | | | | 170 | | | | | 175 | | |
| tac | gcc | gga | tta | gct | gga | ttt | tat | ttg | atc | tca | gat | gcg | ttt | gaa | aaa | 576 |
| Tyr | Ala | Gly | Leu | Ala | Gly | Phe | Tyr | Leu | Ile | Ser | Asp | Ala | Phe | Glu | Lys | |
| | | | 180 | | | | | 185 | | | | | 190 | | | |
| tca | cta | gaa | tta | ccg | aag | gat | gag | tat | gat | att | ccg | cta | atg | atc | atg | 624 |
| Ser | Leu | Glu | Leu | Pro | Lys | Asp | Glu | Tyr | Asp | Ile | Pro | Leu | Met | Ile | Met | |
| | | 195 | | | | | 200 | | | | | 205 | | | | |
| gac | cgt | acg | ttt | caa | gag | gat | ggc | gcg | ctg | ttt | tat | cca | agc | aga | cca | 672 |
| Asp | Arg | Thr | Phe | Gln | Glu | Asp | Gly | Ala | Leu | Phe | Tyr | Pro | Ser | Arg | Pro | |
| | 210 | | | | | 215 | | | | | 220 | | | | | |
| aac | aac | acg | cca | gaa | gac | agt | gat | cta | cca | gat | ccg | tct | atc | gtg | ccc | 720 |
| Asn | Asn | Thr | Pro | Glu | Asp | Ser | Asp | Leu | Pro | Asp | Pro | Ser | Ile | Val | Pro | |
| 225 | | | | | 230 | | | | | 235 | | | | | 240 | |
| ttc | ttt | tgc | gga | gaa | acc | att | ttg | gtc | aat | gga | aaa | gta | tgg | cca | tat | 768 |
| Phe | Phe | Cys | Gly | Glu | Thr | Ile | Leu | Val | Asn | Gly | Lys | Val | Trp | Pro | Tyr | |
| | | | | 245 | | | | | 250 | | | | | 255 | | |
| tta | gaa | gta | gaa | cca | cga | aaa | tac | cgt | ttt | cgt | att | tta | aat | gcg | tct | 816 |
| Leu | Glu | Val | Glu | Pro | Arg | Lys | Tyr | Arg | Phe | Arg | Ile | Leu | Asn | Ala | Ser | |
| | | | 260 | | | | | 265 | | | | | 270 | | | |
| aat | aca | aga | act | tac | gag | ctg | cat | cta | gac | aac | gat | gcg | acg | att | ttg | 864 |
| Asn | Thr | Arg | Thr | Tyr | Glu | Leu | His | Leu | Asp | Asn | Asp | Ala | Thr | Ile | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| caa | att | gga | tct | gat | ggc | ggc | ttt | tta | cca | aga | cct | gtt | cac | cat | caa | 912 |
| Gln | Ile | Gly | Ser | Asp | Gly | Gly | Phe | Leu | Pro | Arg | Pro | Val | His | His | Gln | |
| | 290 | | | | 295 | | | | | 300 | | | | | | |
| tcc | ttt | acc | att | gct | cct | gct | gaa | cga | ttt | gat | gtg | atc | att | gat | ttt | 960 |
| Ser | Phe | Thr | Ile | Ala | Pro | Ala | Glu | Arg | Phe | Asp | Val | Ile | Ile | Asp | Phe | |
| 305 | | | | | 310 | | | | | 315 | | | | | 320 | |
| tca | gct | tac | gaa | aac | aaa | acg | atc | acc | ctt | aaa | aat | aaa | gct | ggc | tgc | 1008 |
| Ser | Ala | Tyr | Glu | Asn | Lys | Thr | Ile | Thr | Leu | Lys | Asn | Lys | Ala | Gly | Cys | |
| | | | | 325 | | | | | 330 | | | | | 335 | | |
| gga | cag | gaa | gta | aat | cct | gaa | aca | gat | gcc | aac | atc | atg | caa | ttt | aaa | 1056 |
| Gly | Gln | Glu | Val | Asn | Pro | Glu | Thr | Asp | Ala | Asn | Ile | Met | Gln | Phe | Lys | |
| | | | | 340 | | | | | 345 | | | | | 350 | | |
| gtc | aca | cgt | cca | cta | aaa | ggg | aga | gca | cct | aaa | aca | tta | cgg | cct | ata | 1104 |
| Val | Thr | Arg | Pro | Leu | Lys | Gly | Arg | Ala | Pro | Lys | Thr | Leu | Arg | Pro | Ile | |
| | | 355 | | | | | 360 | | | | | 365 | | | | |
| ttc | aaa | ccg | ctt | cca | cca | ctt | cga | cct | agt | cgc | gct | gat | caa | gag | cgt | 1152 |
| Phe | Lys | Pro | Leu | Pro | Pro | Leu | Arg | Pro | Ser | Arg | Ala | Asp | Gln | Glu | Arg | |
| | 370 | | | | | 375 | | | | | 380 | | | | | |
| acg | ctc | act | ctt | act | ggt | aca | cag | gat | aaa | tac | ggt | cgc | cct | att | tta | 1200 |
| Thr | Leu | Thr | Leu | Thr | Gly | Thr | Gln | Asp | Lys | Tyr | Gly | Arg | Pro | Ile | Leu | |
| 385 | | | | | 390 | | | | | 395 | | | | | 400 | |
| ttg | ctt | gat | aac | cat | ttt | tgg | aat | gac | cct | gtc | acg | gaa | aat | cct | cgg | 1248 |
| Leu | Leu | Asp | Asn | His | Phe | Trp | Asn | Asp | Pro | Val | Thr | Glu | Asn | Pro | Arg | |
| | | | | 405 | | | | | 410 | | | | | 415 | | |
| ctt | ggc | agt | gta | gag | gtt | tgg | tcc | atc | gtc | aat | cca | aca | agg | ggc | aca | 1296 |
| Leu | Gly | Ser | Val | Glu | Val | Trp | Ser | Ile | Val | Asn | Pro | Thr | Arg | Gly | Thr | |
| | | | 420 | | | | | 425 | | | | | 430 | | | |
| cat | ccc | att | cat | tta | cat | ctt | gtt | caa | ttt | agg | gtg | ata | gac | aga | aga | 1344 |
| His | Pro | Ile | His | Leu | His | Leu | Val | Gln | Phe | Arg | Val | Ile | Asp | Arg | Arg | |
| | | 435 | | | | | 440 | | | | | 445 | | | | |
| cca | ttt | gat | aca | gag | gtc | tat | caa | tcg | aca | ggg | gac | att | gtg | tat | aca | 1392 |
| Pro | Phe | Asp | Thr | Glu | Val | Tyr | Gln | Ser | Thr | Gly | Asp | Ile | Val | Tyr | Thr | |
| | 450 | | | | | 455 | | | | | 460 | | | | | |
| gga | ccg | aac | gaa | gcc | cct | cct | tta | cat | gaa | caa | ggc | tac | aag | gac | acc | 1440 |
| Gly | Pro | Asn | Glu | Ala | Pro | Pro | Leu | His | Glu | Gln | Gly | Tyr | Lys | Asp | Thr | |
| 465 | | | | | 470 | | | | | 475 | | | | | 480 | |
| att | caa | gcg | cat | gcc | ggt | gaa | gtc | att | cga | atc | att | gct | cgc | ttt | gtt | 1488 |
| Ile | Gln | Ala | His | Ala | Gly | Glu | Val | Ile | Arg | Ile | Ile | Ala | Arg | Phe | Val | |
| | | | | 485 | | | | | 490 | | | | | 495 | | |
| cca | tac | agc | ggc | agg | tac | gtg | tgg | cat | tgt | cat | ata | tta | gag | cac | gag | 1536 |
| Pro | Tyr | Ser | Gly | Arg | Tyr | Val | Trp | His | Cys | His | Ile | Leu | Glu | His | Glu | |
| | | | 500 | | | | | 505 | | | | | 510 | | | |
| gat | tat | gac | atg | atg | agg | ccg | atg | gat | att | att | ctc | gag | cac | cac | cac | 1584 |
| Asp | Tyr | Asp | Met | Met | Arg | Pro | Met | Asp | Ile | Ile | Leu | Glu | His | His | His | |
| | | | | 515 | | | | | 520 | | | | | 525 | | |
| cac | cac | cac | | | | | | | | | | | | | | 1593 |
| His | His | His | | | | | | | | | | | | | | |
| | 530 | | | | | | | | | | | | | | | |

<210> SEQ ID NO 2
<211> LENGTH: 531
<212> TYPE: PRT
<213> ORGANISM: Bacillus pumilus

<400> SEQUENCE: 2

Met Ala Ser Met Thr Gly Gly Gln Gln Met Gly Arg Gly Ser Met Asn
1               5                   10                  15

Leu Glu Lys Phe Val Asp Glu Leu Pro Ile Pro Glu Val Ala Glu Pro
            20                  25                  30

-continued

```
Val Lys Lys Asn Pro Arg Gln Thr Tyr Tyr Glu Ile Ala Met Glu Glu
             35                  40                  45

Val Phe Leu Lys Val His Arg Asp Leu Pro Pro Thr Lys Leu Trp Thr
 50                  55                  60

Tyr Asn Gly Ser Leu Pro Gly Pro Thr Ile His Ala Asn Arg Asn Glu
 65                  70                  75                  80

Lys Val Lys Val Lys Trp Met Asn Lys Leu Pro Leu Lys His Phe Leu
                 85                  90                  95

Pro Val Asp His Thr Ile His Glu Gly His His Asp Glu Pro Glu Val
             100                 105                 110

Lys Thr Val Val His Leu His Gly Gly Val Thr Pro Ala Ser Ser Asp
             115                 120                 125

Gly Tyr Pro Glu Ala Trp Phe Ser Arg Asp Phe Glu Ala Thr Gly Pro
 130                 135                 140

Phe Phe Glu Arg Glu Val Tyr Glu Tyr Pro Asn His Gln Gln Ala Cys
145                 150                 155                 160

Thr Leu Trp Tyr His Asp His Ala Met Ala Leu Thr Arg Leu Asn Val
                 165                 170                 175

Tyr Ala Gly Leu Ala Gly Phe Tyr Leu Ile Ser Asp Ala Phe Glu Lys
             180                 185                 190

Ser Leu Glu Leu Pro Lys Asp Glu Tyr Asp Ile Pro Leu Met Ile Met
             195                 200                 205

Asp Arg Thr Phe Gln Glu Asp Gly Ala Leu Phe Tyr Pro Ser Arg Pro
             210                 215                 220

Asn Asn Thr Pro Glu Asp Ser Asp Leu Pro Asp Pro Ser Ile Val Pro
225                 230                 235                 240

Phe Phe Cys Gly Glu Thr Ile Leu Val Asn Gly Lys Val Trp Pro Tyr
                 245                 250                 255

Leu Glu Val Glu Pro Arg Lys Tyr Arg Phe Arg Ile Leu Asn Ala Ser
             260                 265                 270

Asn Thr Arg Thr Tyr Glu Leu His Leu Asp Asn Asp Ala Thr Ile Leu
             275                 280                 285

Gln Ile Gly Ser Asp Gly Gly Phe Leu Pro Arg Pro Val His His Gln
 290                 295                 300

Ser Phe Thr Ile Ala Pro Ala Glu Arg Phe Asp Val Ile Ile Asp Phe
305                 310                 315                 320

Ser Ala Tyr Glu Asn Lys Thr Ile Thr Leu Lys Asn Lys Ala Gly Cys
                 325                 330                 335

Gly Gln Glu Val Asn Pro Glu Thr Asp Ala Asn Ile Met Gln Phe Lys
             340                 345                 350

Val Thr Arg Pro Leu Lys Gly Arg Ala Pro Lys Thr Leu Arg Pro Ile
             355                 360                 365

Phe Lys Pro Leu Pro Pro Leu Arg Pro Ser Arg Ala Asp Gln Glu Arg
             370                 375                 380

Thr Leu Thr Leu Thr Gly Thr Gln Asp Lys Tyr Gly Arg Pro Ile Leu
385                 390                 395                 400

Leu Leu Asp Asn His Phe Trp Asn Asp Pro Val Thr Glu Asn Pro Arg
                 405                 410                 415

Leu Gly Ser Val Glu Val Trp Ser Ile Val Asn Pro Thr Arg Gly Thr
             420                 425                 430

His Pro Ile His Leu His Leu Val Gln Phe Arg Val Ile Asp Arg Arg
             435                 440                 445
```

-continued

```
Pro Phe Asp Thr Glu Val Tyr Gln Ser Thr Gly Asp Ile Val Tyr Thr
    450                 455                 460

Gly Pro Asn Glu Ala Pro Pro Leu His Glu Gln Gly Tyr Lys Asp Thr
465                 470                 475                 480

Ile Gln Ala His Ala Gly Glu Val Ile Arg Ile Ala Arg Phe Val
                485                 490                 495

Pro Tyr Ser Gly Arg Tyr Val Trp His Cys His Ile Leu Glu His Glu
            500                 505                 510

Asp Tyr Asp Met Met Arg Pro Met Asp Ile Ile Leu Glu His His His
            515                 520                 525

His His His
        530

<210> SEQ ID NO 3
<211> LENGTH: 36
<212> TYPE: DNA
<213> ORGANISM: Bacillus pumilus

<400> SEQUENCE: 3
catggatcca tgaacctaga aaaatttgtt gacgag                       36

<210> SEQ ID NO 4
<211> LENGTH: 36
<212> TYPE: DNA
<213> ORGANISM: Bacillus pumilus

<400> SEQUENCE: 4
tacctcgaga ataatatcca tcggcctcat catgtc                       36

<210> SEQ ID NO 5
<211> LENGTH: 1530
<212> TYPE: DNA
<213> ORGANISM: Bacillus pumilus
<220> FEATURE:
<221> NAME/KEY: CDS
<222> LOCATION: (1)..(1530)

<400> SEQUENCE: 5 atg aac cta gaa aaa ttt gtt gac gag ctg cca att cca gaa gtt gcg     48
Met Asn Leu Glu Lys Phe Val Asp Glu Leu Pro Ile Pro Glu Val Ala
1               5                  10                  15 aag ccc gtc aaa aag aac cca aaa caa acg tat tat gaa atc gct atg     96
Lys Pro Val Lys Lys Asn Pro Lys Gln Thr Tyr Tyr Glu Ile Ala Met
            20                  25                  30 gag gag gta ttt cta aaa gtt cat aga gat ctg ccc cca acc aag cta    144
Glu Glu Val Phe Leu Lys Val His Arg Asp Leu Pro Pro Thr Lys Leu
        35                  40                  45 tgg acc tat aat ggc agt ttg cct ggt cca acc att cat gcg aat cga    192
Trp Thr Tyr Asn Gly Ser Leu Pro Gly Pro Thr Ile His Ala Asn Arg
    50                  55                  60 aat gaa aaa gtc aaa gtg aaa tgg atg aac aaa ttg cca ctt aag cat    240
Asn Glu Lys Val Lys Val Lys Trp Met Asn Lys Leu Pro Leu Lys His
65                  70                  75                  80 ttt cta ccg gtc gat cac acc att cac gaa ggc cat cat gat gaa cca    288
Phe Leu Pro Val Asp His Thr Ile His Glu Gly His His Asp Glu Pro
                85                  90                  95 gaa gtt aaa acc gtc gtt cat tta cat ggt ggc gtc aca cca gca agc    336
Glu Val Lys Thr Val Val His Leu His Gly Gly Val Thr Pro Ala Ser
            100                 105                 110
```

```
agt gat ggc tat cca gag gct tgg ttt tca cga gac ttt gaa gca acc       384
Ser Asp Gly Tyr Pro Glu Ala Trp Phe Ser Arg Asp Phe Glu Ala Thr
        115                 120                 125 ggc ccc ttc ttt gaa cgg gag gtg tac gaa tac cca aat cat cag caa       432
Gly Pro Phe Phe Glu Arg Glu Val Tyr Glu Tyr Pro Asn His Gln Gln
130                 135                 140 gcc tgc aca ttg tgg tat cac gat cat gcg atg gca ttg aca cga tta       480
Ala Cys Thr Leu Trp Tyr His Asp His Ala Met Ala Leu Thr Arg Leu
145                 150                 155                 160 aat gtg tat gcc ggc tta gct gga ttt tat ttg atc tca gat gcg ttt       528
Asn Val Tyr Ala Gly Leu Ala Gly Phe Tyr Leu Ile Ser Asp Ala Phe
                165                 170                 175 gaa aag tcg cta gaa tta ccg aag ggt gag tat gat att ccg cta atg       576
Glu Lys Ser Leu Glu Leu Pro Lys Gly Glu Tyr Asp Ile Pro Leu Met
            180                 185                 190 atc atg gac cgt acg ttt cag gag gat ggc gca ctg ttt tat cca agc       624
Ile Met Asp Arg Thr Phe Gln Glu Asp Gly Ala Leu Phe Tyr Pro Ser
        195                 200                 205 agg cca aac aac aca cca gaa gac agt gac ata cca gat ccg tct atc       672
Arg Pro Asn Asn Thr Pro Glu Asp Ser Asp Ile Pro Asp Pro Ser Ile
210                 215                 220 gtg cct ttc ttt tgc gga gaa acc att ttg gtc aat gga aaa gta tgg       720
Val Pro Phe Phe Cys Gly Glu Thr Ile Leu Val Asn Gly Lys Val Trp
225                 230                 235                 240 ccg tat tta gaa gta gag ccg cga aaa tat cgt ttt cgt att tta aat       768
Pro Tyr Leu Glu Val Glu Pro Arg Lys Tyr Arg Phe Arg Ile Leu Asn
                245                 250                 255 gct tcc aat aca aga act tac gag ctg cat cta gac aac gat gcg acg       816
Ala Ser Asn Thr Arg Thr Tyr Glu Leu His Leu Asp Asn Asp Ala Thr
            260                 265                 270 att ttg caa att gga tct gat ggc ggc ttt tta cca aga cct gtt cac       864
Ile Leu Gln Ile Gly Ser Asp Gly Gly Phe Leu Pro Arg Pro Val His
        275                 280                 285 cat caa tcc ttt agc att gct cct gct gaa cga ttt gat gtc atc atc       912
His Gln Ser Phe Ser Ile Ala Pro Ala Glu Arg Phe Asp Val Ile Ile
290                 295                 300 gat ttt tca gct tac gaa aac aaa acg atc acc ctt aaa aat aaa gcc       960
Asp Phe Ser Ala Tyr Glu Asn Lys Thr Ile Thr Leu Lys Asn Lys Ala
305                 310                 315                 320 ggc tgc gga cag gaa gta aat cct gaa aca gat gca aac atc atg caa      1008
Gly Cys Gly Gln Glu Val Asn Pro Glu Thr Asp Ala Asn Ile Met Gln
                325                 330                 335 ttt aaa gtc act cga ccg cta aaa ggg aga gca cct aaa aca tta cgg      1056
Phe Lys Val Thr Arg Pro Leu Lys Gly Arg Ala Pro Lys Thr Leu Arg
            340                 345                 350 cct att ttc aaa ccg ctt cca cca ctt cgg cct tgt cga gct gat aaa      1104
Pro Ile Phe Lys Pro Leu Pro Pro Leu Arg Pro Cys Arg Ala Asp Lys
        355                 360                 365 gag cgt acg ctc act ctt acc ggt aca cag gat aaa tac ggc cgt cct      1152
Glu Arg Thr Leu Thr Leu Thr Gly Thr Gln Asp Lys Tyr Gly Arg Pro
370                 375                 380 att tta ttg cta gat aac caa ttt tgg aat gac cct gtc acg gaa aat      1200
Ile Leu Leu Leu Asp Asn Gln Phe Trp Asn Asp Pro Val Thr Glu Asn
385                 390                 395                 400 cct cgt ctt ggc agt gtg gag gtt tgg tct atc gtc aat cca aca agg      1248
Pro Arg Leu Gly Ser Val Glu Val Trp Ser Ile Val Asn Pro Thr Arg
                405                 410                 415 ggc aca cat cct att cat tta cac ctt gtt caa ttc aga gtg ata gac      1296
Gly Thr His Pro Ile His Leu His Leu Val Gln Phe Arg Val Ile Asp
            420                 425                 430
```

```
aga aga cca ttt gat act gag gtc tat caa tcg aca ggg gac att gtg    1344
Arg Arg Pro Phe Asp Thr Glu Val Tyr Gln Ser Thr Gly Asp Ile Val
        435                 440                 445 tat aca gga cca aac gaa gca cct ccc tta cat gaa caa ggc tac aag    1392
Tyr Thr Gly Pro Asn Glu Ala Pro Pro Leu His Glu Gln Gly Tyr Lys
    450                 455                 460 gac acc att caa gcg cat gcc ggt gaa gtc att cgg atc atc gct cgc    1440
Asp Thr Ile Gln Ala His Ala Gly Glu Val Ile Arg Ile Ile Ala Arg
465                 470                 475                 480 ttt gtt cca tac agc ggc agg tat gtg tgg cat tgt cat ata tta gag    1488
Phe Val Pro Tyr Ser Gly Arg Tyr Val Trp His Cys His Ile Leu Glu
                485                 490                 495 cac gag gat tat gac atg atg cgg ccg atg gat atc atc cag            1530
His Glu Asp Tyr Asp Met Met Arg Pro Met Asp Ile Ile Gln
            500                 505                 510

<210> SEQ ID NO 6
<211> LENGTH: 510
<212> TYPE: PRT
<213> ORGANISM: Bacillus pumilus

<400> SEQUENCE: 6

Met Asn Leu Glu Lys Phe Val Asp Glu Leu Pro Ile Pro Glu Val Ala
1               5                   10                  15

Lys Pro Val Lys Lys Asn Pro Lys Gln Thr Tyr Tyr Glu Ile Ala Met
            20                  25                  30

Glu Glu Val Phe Leu Lys Val His Arg Asp Leu Pro Pro Thr Lys Leu
        35                  40                  45

Trp Thr Tyr Asn Gly Ser Leu Pro Gly Pro Thr Ile His Ala Asn Arg
    50                  55                  60

Asn Glu Lys Val Lys Val Lys Trp Met Asn Lys Leu Pro Leu Lys His
65                  70                  75                  80

Phe Leu Pro Val Asp His Thr Ile His Glu Gly His His Asp Glu Pro
                85                  90                  95

Glu Val Lys Thr Val Val His Leu His Gly Gly Val Thr Pro Ala Ser
            100                 105                 110

Ser Asp Gly Tyr Pro Glu Ala Trp Phe Ser Arg Asp Phe Glu Ala Thr
        115                 120                 125

Gly Pro Phe Phe Glu Arg Glu Val Tyr Glu Tyr Pro Asn His Gln Gln
    130                 135                 140

Ala Cys Thr Leu Trp Tyr His Asp His Ala Met Ala Leu Thr Arg Leu
145                 150                 155                 160

Asn Val Tyr Ala Gly Leu Ala Gly Phe Tyr Leu Ile Ser Asp Ala Phe
                165                 170                 175

Glu Lys Ser Leu Glu Leu Pro Lys Gly Glu Tyr Asp Ile Pro Leu Met
            180                 185                 190

Ile Met Asp Arg Thr Phe Gln Glu Asp Gly Ala Leu Phe Tyr Pro Ser
        195                 200                 205

Arg Pro Asn Asn Thr Pro Glu Asp Ser Asp Ile Pro Asp Pro Ser Ile
    210                 215                 220

Val Pro Phe Phe Cys Gly Glu Thr Ile Leu Val Asn Gly Lys Val Trp
225                 230                 235                 240

Pro Tyr Leu Glu Val Glu Pro Arg Lys Tyr Arg Phe Arg Ile Leu Asn
                245                 250                 255

Ala Ser Asn Thr Arg Thr Tyr Glu Leu His Leu Asp Asn Asp Ala Thr
            260                 265                 270
```

-continued

```
Ile Leu Gln Ile Gly Ser Asp Gly Gly Phe Leu Pro Arg Pro Val His
        275                 280                 285

His Gln Ser Phe Ser Ile Ala Pro Ala Glu Arg Phe Asp Val Ile Ile
    290                 295                 300

Asp Phe Ser Ala Tyr Glu Asn Lys Thr Ile Thr Leu Lys Asn Lys Ala
305                 310                 315                 320

Gly Cys Gly Gln Glu Val Asn Pro Glu Thr Asp Ala Asn Ile Met Gln
                325                 330                 335

Phe Lys Val Thr Arg Pro Leu Lys Gly Arg Ala Pro Lys Thr Leu Arg
            340                 345                 350

Pro Ile Phe Lys Pro Leu Pro Pro Leu Arg Pro Cys Arg Ala Asp Lys
        355                 360                 365

Glu Arg Thr Leu Thr Leu Thr Gly Thr Gln Asp Lys Tyr Gly Arg Pro
    370                 375                 380

Ile Leu Leu Leu Asp Asn Gln Phe Trp Asn Asp Pro Val Thr Glu Asn
385                 390                 395                 400

Pro Arg Leu Gly Ser Val Glu Val Trp Ser Ile Val Asn Pro Thr Arg
                405                 410                 415

Gly Thr His Pro Ile His Leu His Leu Val Gln Phe Arg Val Ile Asp
            420                 425                 430

Arg Arg Pro Phe Asp Thr Glu Val Tyr Gln Ser Thr Gly Asp Ile Val
            435                 440                 445

Tyr Thr Gly Pro Asn Glu Ala Pro Pro Leu His Glu Gln Gly Tyr Lys
    450                 455                 460

Asp Thr Ile Gln Ala His Ala Gly Glu Val Ile Arg Ile Ile Ala Arg
465                 470                 475                 480

Phe Val Pro Tyr Ser Gly Arg Tyr Val Trp His Cys His Ile Leu Glu
                485                 490                 495

His Glu Asp Tyr Asp Met Met Arg Pro Met Asp Ile Ile Gln
            500                 505                 510
```